United States Patent
Li et al.

(10) Patent No.: US 6,911,349 B2
(45) Date of Patent: Jun. 28, 2005

(54) EVALUATING SIDEWALL COVERAGE IN A SEMICONDUCTOR WAFER

(75) Inventors: Jiping Li, Fremont, CA (US); Peter G. Borden, San Mateo, CA (US)

(73) Assignee: Boxer Cross Inc., Santa Clara, CA (US)

( * ) Notice: Subject to any disclaimer, the term of this patent is extended or adjusted under 35 U.S.C. 154(b) by 94 days.

(21) Appl. No.: 09/788,273

(22) Filed: Feb. 16, 2001

(65) Prior Publication Data

US 2002/0151092 A1 Oct. 17, 2002

(51) Int. Cl.[7] .......................... G01R 31/26; H01L 21/66
(52) U.S. Cl. ............................... 438/16; 438/7; 438/14
(58) Field of Search .................................. 438/7, 14, 16, 438/FOR 142

(56) References Cited

U.S. PATENT DOCUMENTS

| | | | |
|---|---|---|---|
| 3,462,602 A | 8/1969 | Apple | 250/83.3 |
| 3,803,413 A | 4/1974 | Vanzetti et al. | 250/338 |
| 3,909,602 A | 9/1975 | Micka | 235/151.3 |
| 3,930,730 A | 1/1976 | Laurens et al. | 356/106 |
| 4,201,087 A | 5/1980 | Akita et al. | 73/339 |
| 4,243,327 A | 1/1981 | Frosch et al. | 356/432 |
| 4,255,971 A | 3/1981 | Rosencwaig | 73/606 |
| 4,273,421 A | 6/1981 | Gurtler | 356/432 |
| 4,455,741 A | 6/1984 | Kolodner | 29/574 |
| 4,466,748 A | 8/1984 | Needham | 374/129 |
| 4,468,136 A | 8/1984 | Murphy et al. | 374/45 |
| 4,521,118 A | 6/1985 | Rosencwaig | 374/5 |
| 4,522,510 A | 6/1985 | Rosencwaig | 374/7 |
| 4,579,463 A | 4/1986 | Rosencwaig et al. | 374/57 |
| 4,632,561 A | 12/1986 | Rosencwaig et al. | 356/432 |
| 4,634,290 A | 1/1987 | Rosencwaig | 374/5 |
| 4,636,088 A | 1/1987 | Rosencwaig et al. | 374/5 |

(Continued)

FOREIGN PATENT DOCUMENTS

| | | | |
|---|---|---|---|
| EP | 0 718 595 | 6/1996 | G01B/11/06 |
| JP | 05006929 A * | 1/1993 | H01L/21/66 |
| JP | 2000009443 A | 1/2000 | G01B/11/24 |
| WO | WO 97/08536 | 3/1997 | G01N/21/00 |

OTHER PUBLICATIONS

Amirtharaj and Seiler, "Optical Properties of Semiconductors," Handbook of Optics, vol. II, McGraw–Hill, Inc., 1995, pp. 36.67–36.68, 36.95 and Table 11. (Exerpt).

Borden, Peter G. et al., "Evaluating A Property of A Multilayered Structure," U.S. Appl. No. 09/521,232, filed on Mar. 8, 2000.

(Continued)

*Primary Examiner*—George Fourson
*Assistant Examiner*—Michelle Estrada
(74) *Attorney, Agent, or Firm*—Silicon Valley Patent Group LLP

(57) ABSTRACT

A sidewall or other feature in a semiconductor wafer is evaluated by illuminating the wafer with at least one beam of electromagnetic radiation, and measuring intensity of a portion of the beam reflected by the wafer. Change in reflectance between measurements provides a measure of a property of the feature. The change may be either a decrease in reflectance or an increase in reflectance, depending on the embodiment. A single beam may be used if it is polarized in a direction substantially perpendicular to a longitudinal direction of the sidewall. A portion of the energy of the beam is absorbed by the sidewall, thereby to cause a decrease in reflectance when compared to reflectance by a flat region. Alternatively, two beams may be used, of which a first beam applies heat to the feature itself or to a region adjacent to the feature, and a second beam is used to measure an increase in reflectance caused by an elevation in temperature due to heat transfer through the feature. The elevation in temperature that is measured can be either of the feature itself, or of a region adjacent to the feature.

39 Claims, 13 Drawing Sheets

U.S. PATENT DOCUMENTS

| | | | |
|---|---|---|---|
| 4,679,946 A | 7/1987 | Rosencwaig et al. ......... 374/5 |
| 4,710,030 A | 12/1987 | Tauc et al. ................. 356/445 |
| 4,750,822 A | 6/1988 | Rosencwaig et al. ....... 356/445 |
| 4,795,260 A | 1/1989 | Schuur et al. .............. 356/400 |
| 4,854,710 A | 8/1989 | Opsal et al. ................ 356/432 |
| 4,950,990 A | 8/1990 | Moulder et al. ........... 324/224 |
| 4,952,063 A | 8/1990 | Opsal et al. ................ 356/432 |
| 4,975,141 A | * 12/1990 | Greco et al. ................. 216/60 |
| 4,996,659 A | 2/1991 | Yamaguchi et al. ....... 364/579 |
| 5,042,951 A | 8/1991 | Gold et al. ................. 356/369 |
| 5,042,952 A | 8/1991 | Opsal et al. ................ 356/432 |
| 5,074,669 A | 12/1991 | Opsal ........................ 356/447 |
| 5,128,864 A | 7/1992 | Waggener et al. ..... 364/413.21 |
| 5,149,978 A | 9/1992 | Opsal et al. ................ 250/234 |
| 5,159,412 A | 10/1992 | Willenberg et al. ........ 356/445 |
| 5,181,080 A | 1/1993 | Fanton et al. .............. 356/381 |
| 5,228,776 A | 7/1993 | Smith et al. .................... 374/5 |
| 5,304,931 A | 4/1994 | Flamig et al. ............. 324/309 |
| 5,377,006 A | 12/1994 | Nakata ...................... 356/349 |
| 5,379,109 A | 1/1995 | Gaskill et al. .............. 356/445 |
| 5,408,327 A | 4/1995 | Geiler et al. ................ 356/432 |
| 5,430,548 A | 7/1995 | Hiroi et al. ................. 356/394 |
| 5,454,004 A | * 9/1995 | Leger .......................... 372/99 |
| 5,574,562 A | 11/1996 | Fishman et al. ........... 356/432 |
| 5,652,716 A | 7/1997 | Battersby ................... 364/578 |
| 5,657,754 A | 8/1997 | Rosencwaig ............... 128/633 |
| 5,667,300 A | 9/1997 | Mandelis et al. ............ 374/43 |
| 5,706,094 A | 1/1998 | Maris ......................... 356/432 |
| 5,741,614 A | * 4/1998 | McCoy et al. ............... 430/30 |
| 5,761,082 A | 6/1998 | Miura-Mattausch ....... 364/490 |
| 5,764,363 A | 6/1998 | Ooki et al. ................. 356/364 |
| 5,790,251 A | 8/1998 | Hagiwara ................... 356/351 |
| 5,877,860 A | 3/1999 | Borden ....................... 356/376 |
| 5,883,518 A | 3/1999 | Borden ....................... 324/752 |
| 5,966,019 A | 10/1999 | Borden ....................... 324/752 |
| 5,978,074 A | 11/1999 | Opsal et al. ................. 356/72 |
| 6,020,964 A | * 2/2000 | Loopstra et al. ............ 356/500 |
| 6,049,220 A | 4/2000 | Borden et al. .............. 324/765 |
| 6,054,868 A | 4/2000 | Borden et al. .............. 324/752 |
| 6,081,334 A | * 6/2000 | Grimbergen et al. ....... 356/499 |
| 6,118,533 A | 9/2000 | Banet et al. ................ 356/345 |
| 6,154,280 A | 11/2000 | Borden ....................... 356/376 |
| 6,169,601 B1 | 1/2001 | Eremin et al. ........... 356/239.8 |
| 6,178,020 B1 | 1/2001 | Schultz et al. ............. 359/107 |
| 6,243,199 B1 | * 6/2001 | Hansen et al. ............. 359/486 |
| 6,281,027 B1 | * 8/2001 | Wei et al. ..................... 438/14 |
| 6,323,951 B1 | 11/2001 | Borden et al. .............. 356/502 |
| 6,327,035 B1 | * 12/2001 | Li et al. ...................... 356/432 |
| 6,330,361 B1 | 12/2001 | Mitchell et al. ............ 382/211 |
| 6,336,969 B1 | * 1/2002 | Yamaguchi et al. ........... 117/7 |
| 6,395,563 B1 | * 5/2002 | Eriguchi ....................... 438/7 |
| 6,400,454 B1 | * 6/2002 | Noguchi et al. ......... 356/237.3 |
| 6,426,644 B1 | 7/2002 | Borden et al. .............. 324/765 |
| 6,483,594 B2 | 11/2002 | Borden et al. .............. 356/502 |
| 6,486,965 B1 | * 11/2002 | Kim .......................... 356/626 |
| 6,489,624 B1 | * 12/2002 | Ushio et al. ........... 250/559.27 |
| 6,489,801 B1 | 12/2002 | Borden et al. .............. 324/766 |
| 6,525,818 B1 | * 2/2003 | Yin et al. .................... 356/400 |
| 6,528,333 B1 | * 3/2003 | Jun et al. ...................... 438/16 |
| 6,559,942 B2 | * 5/2003 | Sui et al. ..................... 356/369 |
| 6,694,284 B1 | 2/2004 | Nikoonahad et al. ....... 702/155 |
| 6,734,968 B1 | 5/2004 | Wang et al. ................ 356/369 |
| 2001/0015937 A1 | * 8/2001 | Yamaguchi et al. .......... 369/13 |
| 2002/0126732 A1 | 9/2002 | Shakouri et al. ............ 374/130 |
| 2002/0186045 A1 | 12/2002 | Cox ............................ 326/41 |
| 2003/0036231 A1 | 2/2003 | Bhattacharva et al. ...... 438/201 |
| 2003/0096436 A1 | 5/2003 | Satya et al. .................. 438/11 |
| 2003/0155927 A1 | 8/2003 | Pinto et al. ................. 324/501 |

OTHER PUBLICATIONS

Eikelboom, J.A. et al., "Microwave Detection of Minority Carriers in Solar Cell Silicon Wafers," *Solar* Energy Materials and Solar Cells, Elsevier Science B. V., Oct. 1995, pp. 169–185.

Grove, A.S., "Physics and Technology of Semiconductor Devices," John Wiley & Sons, Inc., 1967, p. 326.

Jackson, John David, "Classical Electrodynamics," John Wiley & Sons, Inc., 1962, pp. 222–226.

Kolzer, J. et al., "Thermal Imaging and Measurement Techniques for Electronic Materials and Devices," Microelectronics Engineering, vol. 31, 1996, pp. 251–270, XP004006637, Elsevier Publishers BV., Amsterdam, NL, ISSN: 0167–9317.

Martinsons, Christophe et al., "Recent progress in the measurement of the thermal properties of hard coatings," Thin Solid Films, vol. 317, Apr. 1998, pp. 455–457, XP004147705, Elsevier, Sequoia S.A. Lausanne, CH, ISSN: 0040–6090.

Opsal et al., "Thermal–Wave Detection and Thin–Film Thickness Measurements with Laser Beam Deflection," Applied Optics, vol. 22, No. 20, Oct. 1983, pp. 3169–3176.

Orton, J.W. et al., "The Electrical Characterization of Semiconductors: Measurement of Minority Carrier Properties," Academic Press, 1990, pp. 94–100.

Paquin, "Properties of Metals," Handbook of Optics, vol. II, McGraw–Hill, Inc., 1995, pp. 35.3–35.7 (Exerpt).

Rosencwaig, Allan et al., "Detection of thermal waves through optical reflection," Appl. Phys. Lett. 46, Jun. 1985, pp. 1013–1015.

Rosencwaig, Allan, "Thermal Wave Characterization and Inspection of Semiconductor Materials and Devices," Photoacoustic and Thermal Wave Phenomena in Semiconductors, Chapter 5, pp. 97–135, North–Holland, 1987.

Rosencwaig, Allan, "Thermal–Wave Imaging," Science, vol. 218, No. 4569, Oct. 1982, pp. 223–228.

Schroder, Dieter K., "Semiconductor Material and Device Characterization," John Wiley & Sons, Inc., 1990, pp. 2–20, 84–85, 232–235, 304–306, 364, 367–374, 378–383.

Sze, S.M., "Physics of Semiconductor Devices," John Wiley & Sons, Inc., 1981, pp. 50–51.

"Process Monitoring System," Quantox Product Brochure, 3 pgs.

Bristow, Thomas C. and Dag Lindquist, "Surface Measurements With A Non–Contact Nomarski–Profiling Instrument", Interferometric Metrology, SPIE vol. 816, Aug. 1987, pp. 106–110.

Walter G. Driscoll and William Vaughan, "Handbook of Optics", 1978, pp. 8–42, 8–43, 8–107, and 10–72 to 10–77.

Charles Kittel, "Introduction to Solid State Physics", Fourth Edition, John Wiley & Sons, published prior to Mar. 1, 2002, pp. 262–264.

Rolf E. Hummel, "Electronic Properties of Materials, An Introduction For Engineers", published prior to Mar. 1, 2002, pp. 137–145.

H.S. Carslaw and J.C. Jaeger, "Conduction of Heat In Solids", Second Edition, published prior to Mar. 1, 2002, pp. 64–66.

"Process Monitoring System", Quantox Product Brochure, 3 pages, published prior to Mar. 1, 2002.

S. Wolf and R. N. Tauber, "Silicon Processing For The VLSI Era", vol. 1, 1986, pp. 388–399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820–1824.

Dieter K. Schroder "Semiconductor Material And Device Characterization", John Wiley & Sons, Inc. 1990, pp. 538–561, and 458–466.

Quality Today News, article entitled "In–Line Metrology SEM System with 3D Imaging" dated Jan. 10, 2000 and published at http://www.qualitytoday.com/Jan–00–news/011000–3.htm before Apr. 4, 2001.

"Calibration As Well As Measurement On The Same Workpiece During Fabrication" by Peter G. Borden, Jiping Li and Jon Madsen, U.S. Appl. No. 09/974,571, filed Oct. 9, 2001.

"Identifying Defects In a Conductive Structure Of A Wafer, Based On Heat Transfer Therethrough" by Peter G. Borden and Jiping Li, U.S. Appl. No. 10/090,287, filed Mar. 1, 2002.

Office Action dated Mar. 26, 2003 in U.S. Appl. No. 10/090,287.

"Measurement of Lateral Diffusion of Diffused Layers" by Peter G. Borden, G. Jonathan Kluth and Eric Paton, U.S. Appl. No. 10/253,121, filed Sep. 23, 2002.

Office Action dated Jul. 2, 2002 in U.S. Appl. No. 09/521,232.

Response to Office Action dated Aug. 20, 2002 in U.S. Appl. No. 09/521,232.

Office Action dated Dec. 19, 2002 in U.S. Appl. No. 09/521,232.

Response to Office Action dated May 19, 2003 in U.S. Appl. No. 09/521,232.

"Evaluating A Multi–layered Structure For Voids" by Peter G. Borden and Jiping Li, U.S. Appl. No. 10/090,262, filed Mar. 1, 2002.

Office Action dated Mar. 4, 2003 in U.S. Appl. No. 10/090,262.

Response to Office Action dated May 5, 2003 in U.S. Appl. No. 10/090,262.

Office Action dated May 23, 2003 in U.S. Appl. No. 10/090,262.

"An Apparatus and Method For Measuring A Property Of A Layer In A Multilayered Structure" by Peter G. Borden and Jiping Li, U.S. Appl. No. 10/090,316, filed Mar. 1, 2002.

"Measurement of Lateral Diffusion of Diffused Layers" by Peter G. Borden, U.S. Appl. No. 10/253,119, filed Sep. 23, 2002.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

A. Rosencwaig, "Thermal Wave Measurement of Thin–Film Thickness", 1986 American Chemical Society, pp. 182–191.

A. Rosencwaig et al., "Thin–Film Thickness Measurements with Thermal Waves", Journal De Physique, Oct. 1983, pp. C6–483—C6–489.

W. L. Smith et al. "Thermal–wave Measurements and Monitoring of TaSIx Silicide Film Properties" J. Vac. Technol.B2(4), Oct.–Dec. 1984, pp. 710–713.

A. Salnick et al., "Nonlinear Fundamental Photothermal Response in 3D Geometry: Experimental Results for Tungsten", (believed to be prior to Mar. 1, 2002).

S. Ameri et al., "Photo–Displacement Imaging", Mar. 30, 1981, pp. 337–338.

L. Chen et al., "Thermal Wave Studies of Thin Metal Films Using the Meta–Probe–A New Generation Photothermal System" 25th Review of Progress in QNDE, Snowbird, UT Jul. 19–24, 1998, pp 1–12.

P. Alpern and S. Wurm, "Modulated Optical Reflectance Measurements on Bulk Metals and Thin Metallic Layers", J. Appl. Phys. 66(4), Aug. 15, 1989, pp 1676–1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp 120–131.

A. Rosenwaig, "Process Control In IC Manufacturing With Thermal Waves", Review of Progress in Quantitative Nondestructive Evaluation, vol. 9, 1990, pp 2031–2037.

K. Farnaam, "Measurement of Aluminum Alloy Grain Size on Product Wafers and its Correlation to Device Reliability", 1990 WLR Final Report, pp 97–106.

B.C. Forget et al., "High Resolution AC Temperature Field Imaging", Electronic Letters Sep. 25, 1997, vol. 33 No. 20, pp 1688–1689.

C. Paddock et al., "Transient Thermoreflectance from Metal Films", May 1986 vol. 11, No. 5 Optical Letters, pp 273–275.

C. Paddock et al., "Transient Thermoreflectance from Metal Films", J. Appl. Phys. 60(1), Jul. 1, 1986, pp 285–290.

Per–Eric Nordail et al. "Photothermal Radiometry", Physica Scripts, vol. 20, 659–662, 1979.

A. Rosenwaig, "Thermal Wave Monitoring and Imaging of Electronic Materials and Devices", pp 73–109.

A. Rosenwaig, "Applications of Thermal–Wave Physics to Microelectronics", VLSI Electronics, Microstructure Science vol. 9, 1995, pp 227–288.

W. Lee Smith et al., "Voids, Notches and Micros–cracks in A1 Metallization Detected by Nondestructive Thermal Wave Imaging", Jun. 23, 1989, pp. 211–221.

W. Lee Smith et al., Imaging of Subsurface in ULSI Metalization (A1 Voids SI Precipitates, Silicide Instability) and SI Substrates (D Defects), Technical Proceedings Simicon/Japan 1992, Nippon Convention Center, Japan pp 238–246.

W. Lee Smith, "Nondestructive Thermal Wave Imaging of Voids & Microcracks in Aluminum Metallization", 1989 WLR Final Report, pp 55–68.

W. Lee Smith, "Direct Measurement of Stress–Induced Void Growth by Thermal Wave Modulated Optical Reflectance Imaging", 1991 IEEE/IRPS, pp 200–208.

W. Lee Smith, "Evaluating Voids and Microcracks in A1 Metalization", Semiconductor International, Jan. 1990, pp 232–237.

C. G. Welles et al., "High–Resolution Thermal Wave Imaging of Surface and Subsurface Defects in IC Metal Lines", Materials Research Society, SF Marriott, Apr. 27–May 1, 1992, pp 1187–1191.

L. Fabbri et al., "Analysis of Local Heat Transfer Properties of Tape–cast AIN Ceramics Using Photothermal Reflectance Microscopy", 1996 Chapman & Hall, pp 5429–5436.

J. A. Batista et al., "Biased MOS–FET and Polycrystalline Silicon Tracks Investigated by Photothermal Reflectance Microscopy", pp 468–469.

L. Chen et al., "Meta–Probe: A New Generation Photothermal System For Thin Metal Films Characterization" (believed to be prior to Feb. 16, 2001).

L. Chen et al., "Thermal Wave Studies of Thin Metal Films and Structures", (believed to be prior to Mar. 1, 2002).

9th International Conference on Photoacoustic and Photothermal Phenomena Conference Digest, Jun. 27–30, 1996 Nanjing, P.R. China, pp 81.

R. S. Sharpe, Research Techniques in Nondestructive Testing vol. VII, Academic Press 1984, pp 158–365.

R. L. Thomas et al., "Thermal Wave Imaging For Nondestructive Evaluation" 1982 Ultrasonic Symposium, pp 586–590.

G. Slade Cargill III, "Electron–Acoustic Microscopy", Physics Today, Oct. 1981, pp 27–32.

A. Rosencwaig, "Thermal Wave Microscopy", Solid State Technology, Mar. 1982, pp 91–97.

Eric A. Ash, "Acoustical Imaging" vol. 12, Plenium Press, Jul. 19–22, 1982, pp 61–65.

* cited by examiner

EVALUATING SIDEWALL COVERAGE IN A SEMICONDUCTOR WAFER

CROSS-REFERENCE TO RELATED APPLICATIONS

This application is related to and incorporates by reference herein in their entirety the following commonly owned, U.S. Patent Applications:

Ser. No. 09/095,804 entitled "AN APPARATUS AND METHOD FOR EVALUATING A WAFER OF SEMICONDUCTOR MATERIAL", filed Jun. 10, 1998, by Peter G. Borden et al.;

Ser. No. 09/095,805 entitled "AN APPARATUS AND METHOD FOR MEASURING A PROPERTY OF A LAYER IN A MULTILAYERED STRUCTURE", filed Jun. 10, 1998 by Peter G. Borden et al.; and Ser. No. 09/521,232 entitled "EVALUATING A PROPERTY OF A MULTILAYERED STRUCTURE", filed on Mar. 8, 2000 by Peter G. Borden et al.

BACKGROUND

Damascene structures in semiconductor substrates are so-named because they consist of metal lines formed in narrow grooves. These grooves may be <0.15 $\mu$m wide, and >0.5 $\mu$m deep, with a aspect ratios that may exceed 3:1 (ratio of height to width). Such damascene structures are typically formed in a multi-step process, of the type shown in FIG. 1. First, in step 110, photoresist layer 101 is formed on insulator layer 102 over substrate 103. Insulator 102 is a material such as silicon dioxide, and substrate 103 is silicon. In step 111, photoresist layer 101 is patterned, forming grooves 104a–f. The structure is then etched in step 112, forming grooves 105a–f in the insulator layer 102. Note that the grooves are less deep than the thickness of the insulator 102. The photoresist layer 101 is subsequently stripped. In step 113 the structure is coated with a barrier layer of a metal such as tantalum, followed by a seed layer of a metal such as copper, indicated as combined layers 105bs. The copper seed layer provides a conductive coating to allow electroplating of a thick copper layer onto the structure in step 114, that material being shown as layer 106. The seed layer may be 1000 Å thick on the surface, but only 100–200 Å thick on the walls of the grooves. Similarly, the tantalum layer may be 250 Å thick on the surface, but only 50 Å or less thick on the walls of the grooves. The tantalum layer prevents the copper from diffusing into the underlying layers; hence its name "barrier", and also improves adhesion of the copper to insulator 102. In step 115 the electroplated layer 106 is polished away, leaving a fill of copper in the grooves.

The yield of this process depends on the thickness t of each sidewall of each groove. This is a parameter called sidewall coverage. If the sidewall coverage is too thin, then the coating may be discontinuous, or even non-existent. It then acts as a poor nucleating surface for the subsequent electrodeposition of subsequent thick layer 106, causing problems such as void formation. These voids act as breaks in the metal line, either preventing current flow, or constricting current flow to the point where the line locally overheats and fails. If the coating is too thick, the top of the groove may close off, preventing adequate circulation of electrodeposition electrolyte, resulting in poor filling of the grooves. This problem is further aggravated as the technology advances, and the grooves become deeper and narrower.

A prior art method for measuring sidewall coverage uses transmission electron microscopy (TEM) imaging. In TEM imaging, a sample is prepared, either by using a focused ion beam that etches away a portion of the array, or by cleaving a sample and ion milling it to make it sufficiently thin so that it can be penetrated with high-energy electrons to form a TEM image. This is obviously a destructive method, since a portion of the integrated circuit must be physically removed. It is also slow, because adequate removal of material at any site may take many tens of minutes, and additional sample preparation, mounting and alignment may take hours. Thus, TEM imaging is useful for analytic diagnosis, but, being destructive and slow, is unsuitable for process control.

An abstract of a paper entitled "Mining Diagnostic Information from CD-SEM for Photolithography Control" by Haolin Zhang, available over the Internet at http://buffy.eecs.berkeley.edu/IRO/Summary/98abstracts/chapter5.html states that "Top view CD-SEM is a routine inspection tool in today's fabrication line. Even though relatively accurate critical dimensions can be obtained from a CD-SEM, much more information is hidden in the high resolution SEM images. The digitized SEM scan is a signal that may be used to monitor and diagnose the process sequence. We successfully used SEM traces of small test patterns to correctly infer two critical process parameters: focus distance and exposure dose. Principal component analysis (PCA) is applied to extract the characteristic feature behind the digitized SEM image. A feed-forward neural network trained by back propagation has been implemented to classify the different conditions. The sidewall profile of the pattern can also be studied by similar methodology. We plan to find an appropriate algorithm to relate the top view CD-SEM to the sidewall profile and film thickness. We will use an atomic force microscope (AFM) and/or cross-sectional SEM to extract sidewall information in order to calibrate the model."

The abstract of another paper, entitled "Real Time Monitoring of Grating Structures Using RCWA Modeling and Two-Channel Spectral Reflectometry" by Hsu-Ting Huang et al. available over the Internet at http://www.aps.org/meet/MAR00/baps/abs/S6480.html states "We have previously demonstrated that specular SE or SR data from grating structures can be accurately analyzed using vector diffraction theory (using the rigorous coupled wave analysis method, RCWA) to extract the topography of surface relief gratings on wafers. In ex situ experiments, we have demonstrated that this method accurately yields critical dimensions, feature heights, and wall angles more complex sidewall shape information from deep sub-micron gratings. We have also reported on a high-speed, low-cost optical system, two channel spectroscopic reflectometry (2CSR), for in situ monitoring. Our current 2CSR system simultaneously measures $|R\_p|^2$ and $|R\_s|^2$ over the 370–850 nm spectral range at minimum sampling time of 6 ms. In this talk, we will show the first demonstrations of in situ, real-time monitoring of feature evolution in a reactive ion etching system (RIE). Using 2CSR and RCWA-based analysis we have successfully extracted the critical dimensions, wall shape, and feature height evolution of a 0.35 $\mu$m line/space photoresist grating during an O_2 RIE process. Cross-sectional SEM photos before and after the etch runs will be shown which verify the high accuracy of this method. We will show variations in the topography evolution with changes in the RIE conditions. Measurement sensitivity issues and implications for industrial process control will be discussed."

SUMMARY

In accordance with the invention, a feature (such as a sidewall of a groove or a via hole, and formed of a reflective material) in a semiconductor wafer is evaluated by illuminating the wafer with at least one beam of electromagnetic radiation, and measuring intensity of a portion of the beam reflected by the wafer. Change in reflectance between measurements provides a measure of a property of the feature. The change may be either a decrease in reflectance or an increase in reflectance, depending on the embodiment.

One embodiment uses a single beam that is polarized in a direction substantially perpendicular to a longitudinal direction of the feature. A portion of the energy of the beam is absorbed by the feature, thereby to cause a decrease in reflectance when compared to reflectance of a flat region. A plot of reflectance as a function of distance across a groove, is symmetric when the two sidewalls have identical properties (such as sidewall thickness), and asymmetric when the sidewall coverage differs.

Instead of using a single beam, some embodiments use two beams that may or may not be polarized, and that may or may not form overlapping spots on the wafer. A first beam (called "heating beam") applies heat to the feature itself or to a region adjacent to the feature, and a second beam (called "probe beam") is used to measure an increase in reflectance caused by an elevation in temperature due to heat transfer through the feature. The elevation in temperature that is measured can be either of the feature itself, or of a region adjacent to the feature, depending on the embodiment.

DETAILED DESCRIPTION

Figure 1:
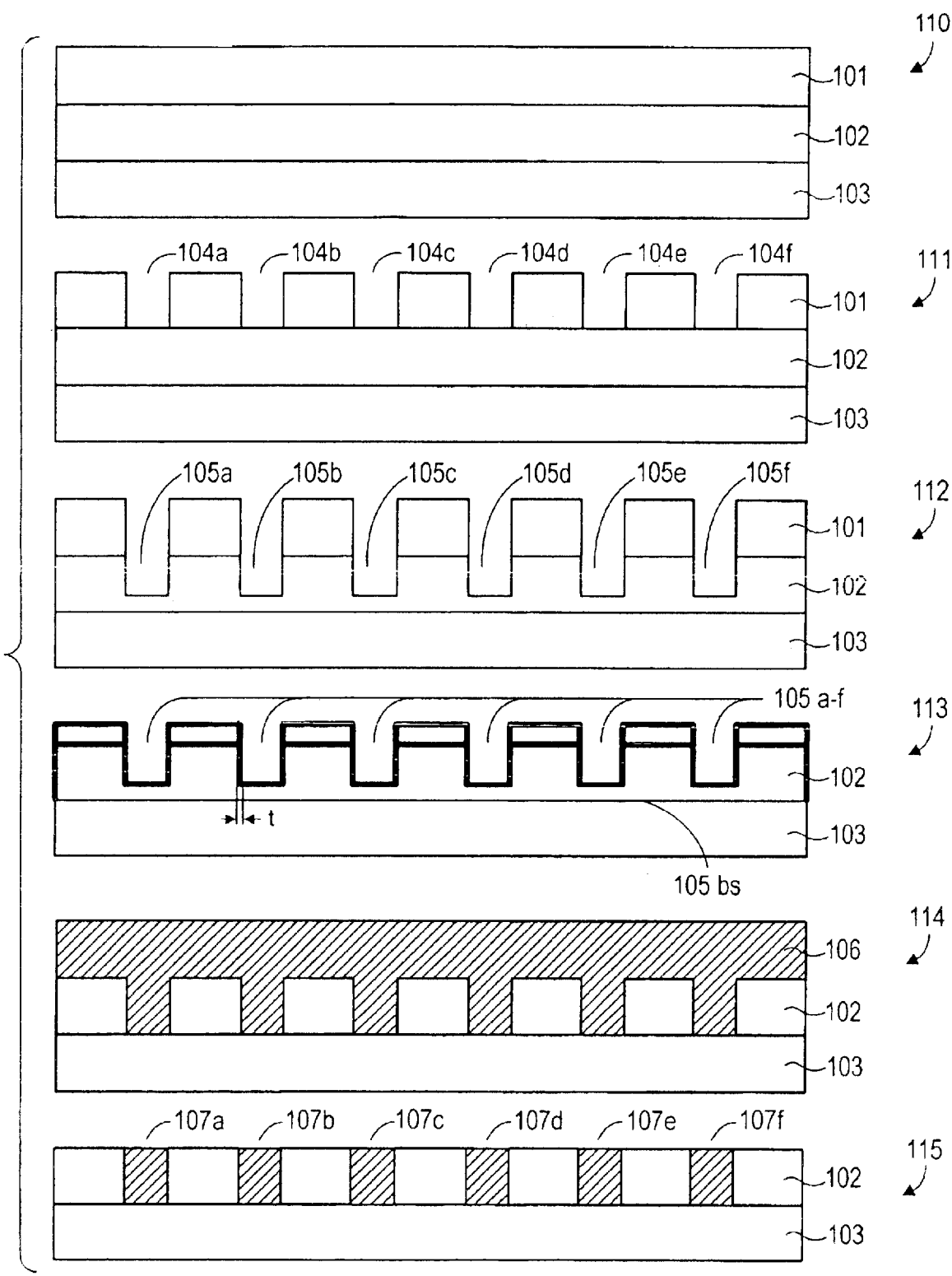
FIG. 1 illustrates a prior art method for fabricating a semiconductor wafer.
Figure 2:
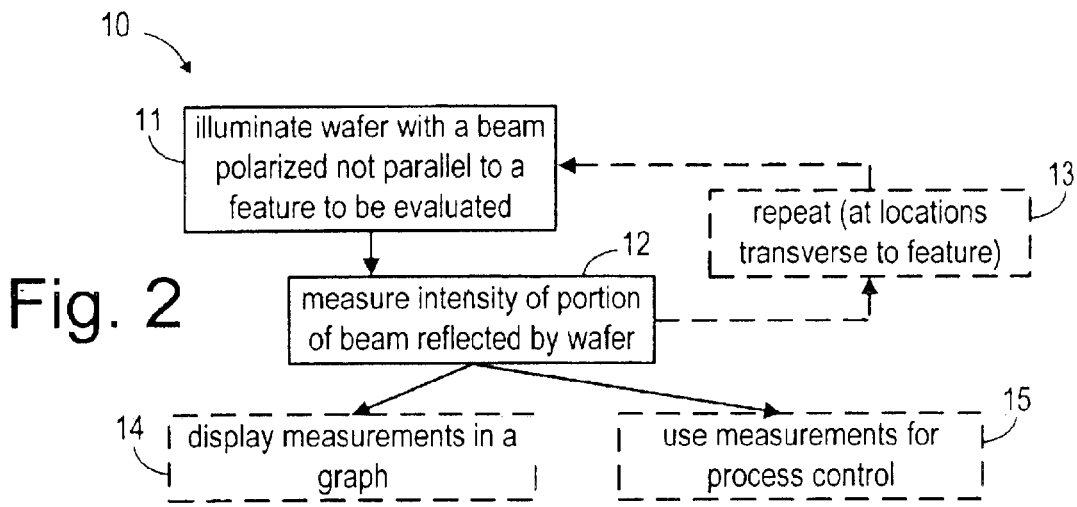
FIGS. 2 and 11 illustrate, in flow charts, acts performed in two embodiments of the invention.

A method 10 (FIG. 2) in accordance with the invention, evaluates a feature 21A in a semiconductor wafer 20 (FIG. 3) by illuminating the wafer 20 (see act 11 in FIG. 2) with a beam 22 of electromagnetic radiation (FIG. 3), and measuring intensity (see act 12) of a portion of the beam 22 reflected by the wafer 20. Such acts 11 and 12 may be repeated (as illustrated by act 13 in FIG. 2), e.g. at a number of positions that are located transverse to feature 21A (or alternatively at positions located in-line with feature 21A). For example, wafer 20 may be displaced in a plane perpendicular to the beam axis, and the beam is held stationary (although in an alternate embodiment, the beam could be moved and the wafer held stationary). For example, the beam is focused on the surface at a point below feature 21A in FIG. 3 and the wafer is moved down in the drawing thereby scanning the beam across the feature and towards the right in FIG. 4 (which shows a cross-sectional view along the direction A—A in FIG. 3), to obtain a set of measurements. The set of measurements includes, in one embodiment, only two measurements (e.g. that are made at equal distances from feature 21A on each side thereof), although in another embodiment a number of such measurements are made in a continuous fashion (in a scanning movement).

A change in intensity of the signal being measured (assuming all parameters (such as intensity of beam 22 incident on wafer 20) are kept constant) provides a measure of a property (such as thickness t) of feature 21A. The change may be either a decrease in reflectance or an increase in reflectance, depending on the embodiment. Therefore, a property of feature 21A is measured by beam 22 in accordance with the invention (by monitoring a change in reflectance) even though beam 22 forms on wafer 20 a spot of diameter D (e.g. 2 μm or 20,000 Å) that is one or more orders of magnitude larger than the thickness t (e.g. 50 Å) of feature 21A. The measurements can be displayed to an operator, e.g. in a graph as illustrated by act 14 in FIG. 2. Alternatively, the measurements can be used automatically, for process control as illustrated by act 15.

Figure 3:
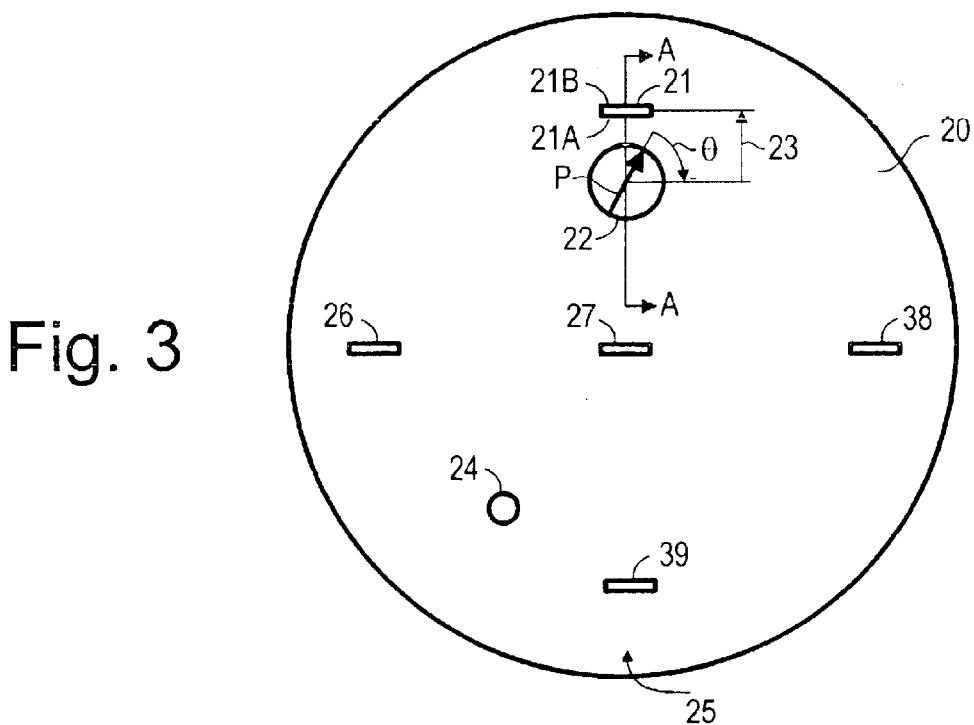
FIG. 3 illustrates, a relationship between polarization of a beam used in an act of FIG. 2 and a longitudinal direction of a feature under evaluation, in a plan view of a semiconductor wafer.
Figure 4:
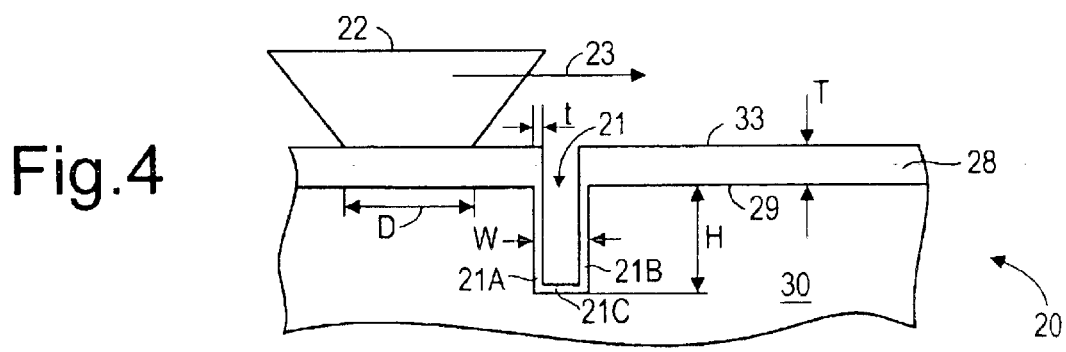
FIG. 4 illustrates, a cross-sectional view of the semiconductor wafer in the direction A—A of FIG. 3.

Feature 21A may be, for example, a sidewall of a groove 21 that has another sidewall 21B separated therefrom by a floor 21C (FIG. 4). Alternatively, feature 21A may be a sidewall of a via hole 24 (FIG. 3). Feature 21A is typically formed of a reflective material that reflects a majority of the incident energy. Although feature 21A is located at the top of wafer 20 relative to a notch 25 therein, such a feature that is being evaluated may be located anywhere in wafer 20, e.g. on the left as illustrated by feature 26 or in the center as illustrated by feature 27. Depending on the circuitry to be formed from wafer 20, such a feature may form a part of such circuitry, or alternatively may be introduced into wafer 20 for evaluation of the fabrication process (i.e. a test feature). Furthermore, depending on the embodiment, feature 21A may be a portion of a larger structure, such as an array as described later on.

In one exemplary wafer 20, sidewalls 21A and 21B are formed by a conductive layer 28 (FIG. 4), of e.g. copper over tantalum, that is also formed over a top surface 29 of a substrate 30. Typical dimensions are as follows. Groove width W is on the order of 0.18 μm (1800 Å) and height H on the order of 0.5 μm (5000 Å). Sidewall 21A has a thickness on the order of 200 Å and thickness T of layer 28 (e.g. of copper) over surface 29 is on the order of 1000 Å.

Measurements of the type described herein provide at least two advantages over prior art methods: (1) the properties of a line of width much smaller than the beam diameter can be measured, and (2) the measurement indicates not only the sidewall coverage but relative coverage of the two walls.

In one embodiment (also called "single beam embodiment"), a feature 21A which is part of groove 21 is illuminated by a beam 22 which is polarized in a direction P. In one implementation of this embodiment, direction P forms an angle θ with a longitudinal direction of feature 21A. For beam 22 to be reflected by groove 21, an electric field must be established in floor 21C that matches the incident electric field. This induced field re-radiates, resulting in a reflected portion of beam 22. When the incident electric field is parallel to groove 21, this occurs, and groove 21 acts like the rest of layer 28, reflecting all of the incident power other than a negligible fraction (e.g. less than 10%) that may be lost at the sidewalls 21A and 21B. Hence, the component of beam 22 that is polarized parallel to groove 21 is reflected. However, when the incident electric field is perpendicular to groove 21, and when groove width W is smaller than the wavelength of beam 22, and groove 21 is too narrow to set up a matching electric field. As a result, the reflection is very small and the component of beam 22 polarized perpendicular to groove 21 transmits as heat into substrate 30, as if groove 21 did not exist.

For this reason, beam 22's polarization direction P is deliberately selected to be not parallel to feature 21A. In the example illustrated in FIG. 3, angle θ>45°. Preferably, but not necessarily, angle θ≅90° (e.g. within 10% which is ±9°). Also, in this embodiment, the wavelength (e.g. 980 nm or 9800 Å) of beam 22 is larger than width W (2000 Å) of the feature (and therefore the spot size is also greater than the width of the feature) so that beam 22 is not reflected by feature 21A in the same manner as a region adjacent to the feature. Instead, at least a portion of the energy of beam 22 is absorbed by feature 21A.

In one implementation of the single beam embodiment, measurements (of a reflected portion of beam 22) are repeatedly made during a scan (also called "transverse scan") across feature 21A, in a direction 23 that is perpendicular to the longitudinal direction of feature 21. The measurements, when plotted as a function of distance yield a curve (called "reflectance curve") which indicates properties across the cross-section of the feature. For example, a reflectance curve 31 (FIG. 5) is symmetric when the two sidewalls 21A and 21B of a groove 21 (FIG. 4) have similar or identical properties (such as sidewall thickness).

In this example, another reflectance curve 32 (FIG. 5) is asymmetric when the sidewall coverage differs for the two sidewalls 21A and 21B, e.g. when groove 21 is located at the top (see FIG. 3) of wafer 20 (relative to notch 25). The asymmetry of curve 32 of this example is manifested in three forms: (a) a valley (minimum) 32V is offset from a center line C of groove 21, (b) slopes on the two sides of the valley are different (with slope of left segment 32L being more gradual than slope of right segment 32R), and (c) left segment 32L is piecewise linear, and has a "knee" 32K (coincidentally at the intersection of curves 31 and 32) whereas right segment 32R is linear. Although three forms of asymmetry are manifested in this example, in other examples only one or two of these forms of asymmetry may be present. Also, depending on the example, other forms of asymmetry may be present as will be apparent to the skilled artisan. As another example, a reflection curve 34 for a groove 26 on the left side of wafer 20 is substantially symmetric. In this example, all three grooves 22, 26 and 27 are parallel to one another, so that groove 21 is oriented perpendicular to a radius vector drawn from a center of the wafer 20, and groove 26 is oriented parallel to the radius vector. Similar reflection curves are obtained for grooves located on the right of wafer 20, and at the bottom (near notch 25) of wafer 20 as illustrated in FIG. 6, described next.

Figure 6:
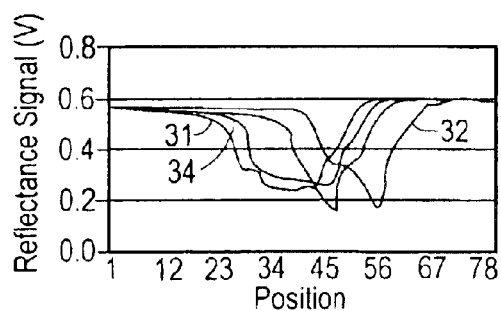

FIG. 6 shows the reflection curves from five grooves at the center and 0°, 90°, 180° and 270° positions, where 0° represents the wafer top, and 180° represents the wafer bottom. In this case, all five grooves are parallel, so that the 0° and 180° grooves are oriented perpendicular to the radius vector and the 90° and 270° grooves are oriented parallel to the radius vector. Such grooves may be formed in wafer 20 as "test" structures, for the purposes of monitoring the efficacy of the fabrication process as described herein. In FIG. 6, the scans are symmetric at the center and when the grooves are parallel to the radius, as in the locations of wafer center, wafer left, and wafer right, and asymmetric when the grooves are perpendicular to the radius and at the wafer periphery, as in locations of wafer top and wafer bottom.

Figure 5:
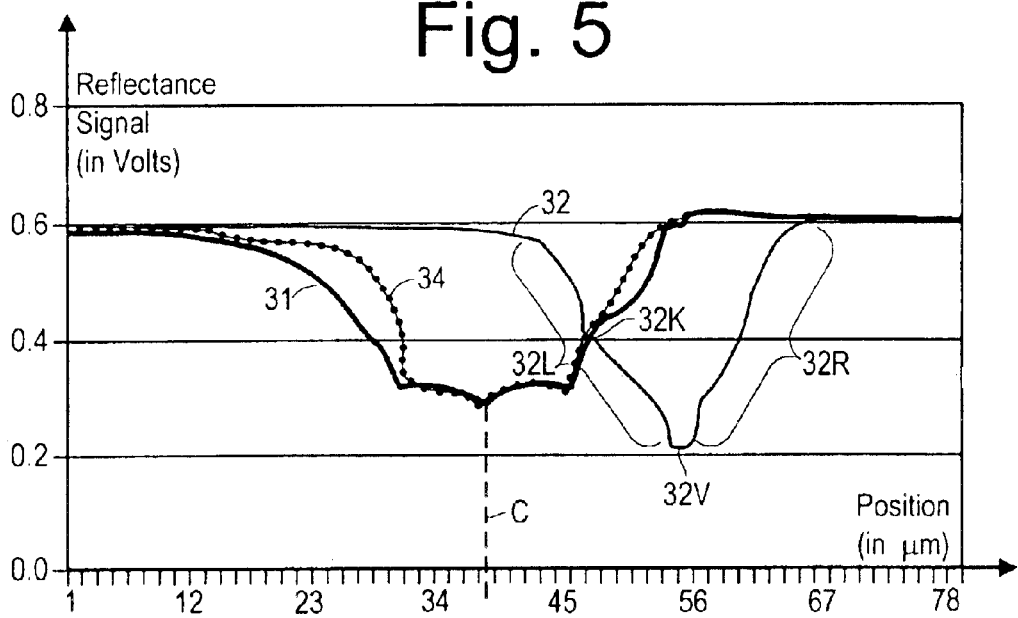
FIGS. 5–10 illustrate, in graphs, change in reflectance as a function of distance, obtained from a scan across a groove in accordance with the invention.

The measurements plotted in FIGS. 5 and 6 were performed with a single laser beam 22 focused on an exposed surface 33 of wafer 20. Beam 22 was polarized with the electric field vector perpendicular to groove 21 (parallel to the scan direction 23). Beam 22 has a wavelength of 0.83 μm and a spot diameter on surface of 33 (FIG. 4) of 1.5 μm. Because of the perpendicular polarization, at least some laser light enters groove 21, which reduces the reflection as beam 22 moves in direction 23 across groove 21. A metal such as copper is highly reflective—on the order of 97%. Therefore, light absorbed in groove 21 measurably reduces the reflected signal. Because width W of groove 21 is small compared to diameter D of laser beam 22, the intensity of the reflection measured through scan in direction 23 (as shown by curve 31 in FIG. 5) matches the intensity profile of beam 22 (which is approximately gaussian) when groove 21 is symmetric.

Figure 7:
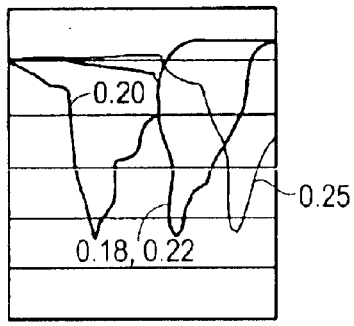
Figure 8:
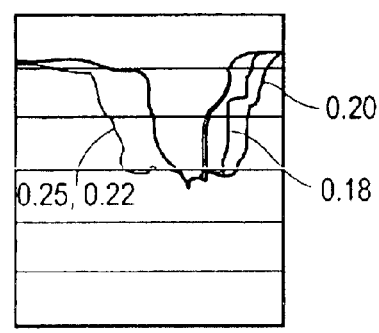
Figure 9:
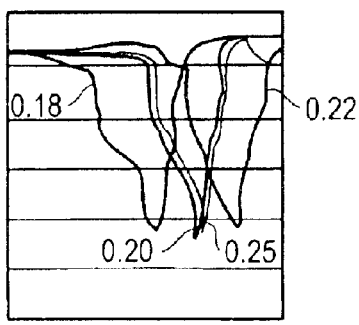

Depending on the process used to form wafer 20, sidewalls 21A and 21B of groove 21 are not symmetric in all locations of wafer 20. Specifically, reflection curves in FIGS. 5–9 were generated by scans across grooves at different locations on wafers whose metal layers were deposited by physical vapor deposition (PVD, also known as sputter deposition). Specifically, FIGS. 7–9 shows scans across single grooves of widths of 0.18, 0.20, 0.22 and 0.25 μm. FIG. 7 illustrates scans across groove 39 near the lower edge of the wafers (near notch 25; see FIG. 3), which are asymmetric. FIG. 8 illustrates scans across a groove at the center of wafers (see groove 27 in FIG. 3), which show symmetry. FIG. 9 illustrates scans across a groove 21 at the top of the wafers, which are asymmetric. The asymmetry in FIGS. 7 and 9 is repeatable and mirrored about the wafer center. Regardless of its position, the grooves 21, 27 and 39 used to generate the reflection curves in FIGS. 7–9 have the same direction, and run perpendicular to the wafer radius vector, and the electric field polarization is parallel to the wafer radius vector.

The reason for the difference in symmetry between the reflection curves of FIGS. 5–9 is explained through understanding of the metal PVD deposition process. The copper is laid down in a sputter coater, with an target electrode above the wafer. By symmetry, the process is most uniform in the center, and least uniform at the edge. Near the edge, the wall of a groove facing the center has greater exposure to deposition than the wall facing away from the center. Thus, the 0° and 180° grooves 21 and 39, which have walls facing to and away from the center, show asymmetry, and the 90° and 270° grooves 38 and 26, which have both walls symmetric with respect to the deposition, show symmetry. Therefore, it is seen that the asymmetric profile indicates asymmetric deposition on the groove walls.

Figure 10:
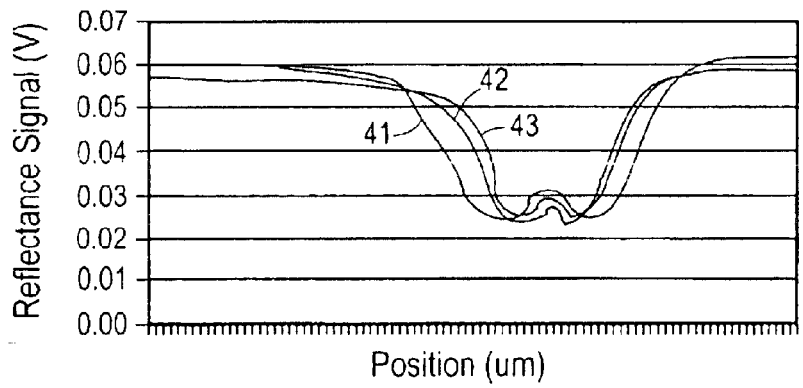

Not all metal depositions show such asymmetry, because different metals are deposited under different conditions. FIG. 10 shows reflection curves 43, 41 and 42 respectively represent measurements from scans across the top, center and bottom (notch) grooves of a wafer having tantalum (no copper) coating. Curves 41–43 are symmetric. This indicates that the asymmetry is not an artifact of the groove shape, but is truly indicative of asymmetric coating of the sidewalls.

Therefore, in one example, reflectance curves of two sidewalls located opposite to one another in a groove are compared to one another, either visually by an operator, or automatically (e.g. by comparison of slopes and/or distance of minimum from center and/or presence of knee) to identify symmetry/asymmetry. Depending on the embodiment, a measure of a sidewall's property can be extracted from a reflectance curve, e.g. the slope of the reflectance curve may be compared to slopes of such curves of wafers having properties determined by a prior art process (such as TEM), to determine sidewall thickness. Computation of slope (or other coefficient of a function fitted to the reflectance curve) is useful in process control, e.g. a process parameter used in formation of the feature on the wafer may be changed, when a limit (on the slope or other coefficient) is crossed.

Determining sidewall coverage as described above using a single probe beam 22 by generating a reflectance curve is feasible during process control because the process is non-destructive and non-contacting, and is sufficiently rapid to provide a high throughput of wafers (e.g. each measurement takes about 5 seconds per site, or for each point in a line scan). In addition, the area required for measurement of a reflectance curve is small—no larger than a few microns—which allows use directly in patterns where only a small number of lines (e.g. one line) are available for measurement, and enables resolution of fine-scale process non-uniformity, and monitoring of localized defects in a sidewall.

A change in reflectance over a feature also provides a measure of a property of the feature in the longitudinal direction, e.g. when scanning along the feature (also called "longitudinal scan"). Therefore, reflectance measurements of the single beam embodiment as described above can also be made in a longitudinal scan, e.g. to monitor uniformity in properties of a sidewall or a trace, along its length. A change in reflectance measurement during the longitudinal scan indicates a change in a property (such as thickness) of the sidewall. Regardless of the scan direction, the beam is polarized in a direction other than parallel to a longitudinal direction of the feature, so that at least a portion of the energy of the beam is absorbed by the feature, thereby to reduce reflectance over the feature.

Although an embodiment using a single beam 22 has been described above in reference to FIGS. 3–10, some embodiments use two beams that may or may not be polarized, and that may or may not form overlapping spots on wafer 20. In two alternative embodiments, a first beam (called "heating beam") applies heat to the feature itself or to a region adjacent to the feature, and a second beam (called "probe beam") is used to measure an increase in reflectance caused by an elevation in temperature due to heat transfer through the feature. The elevation in temperature that is measured can be either of the feature itself, or of a region adjacent to the feature.

Figure 11:
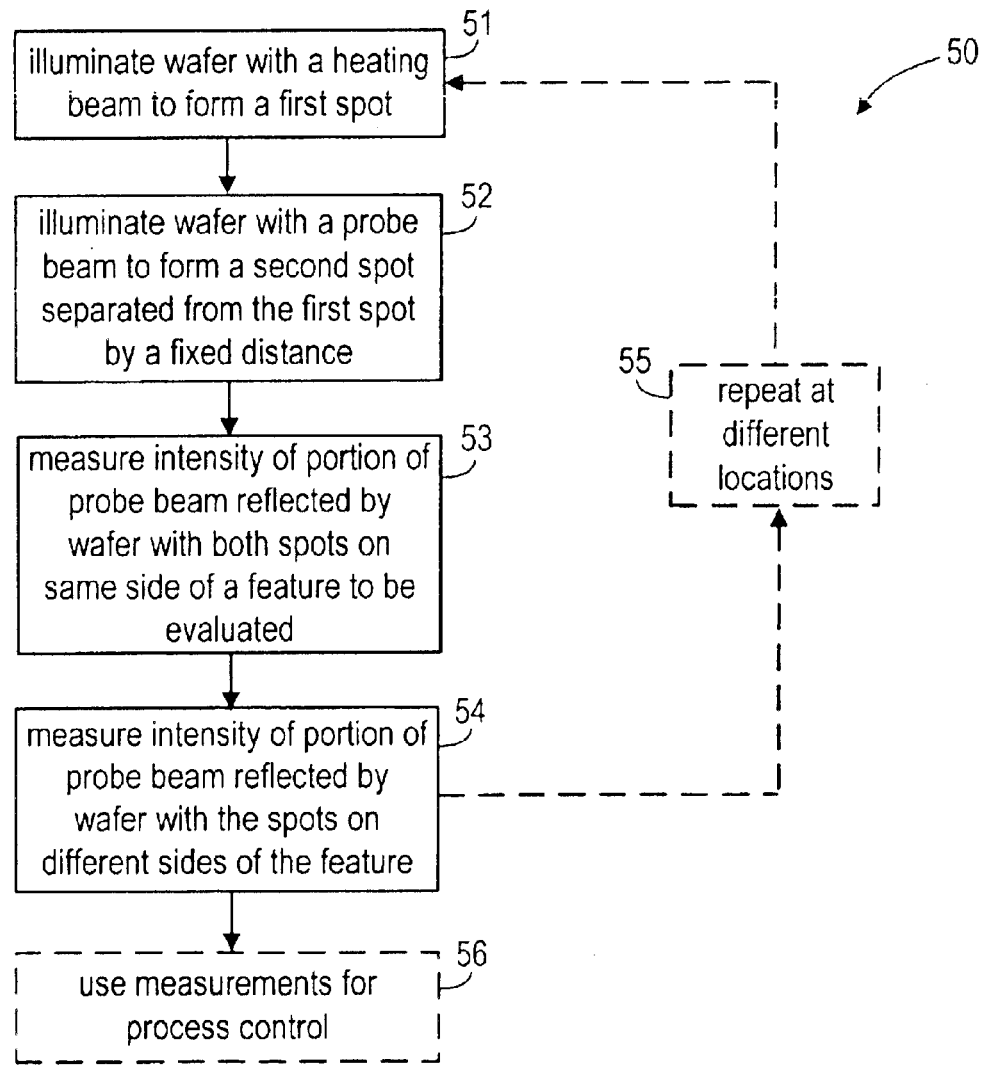
Figure 12:
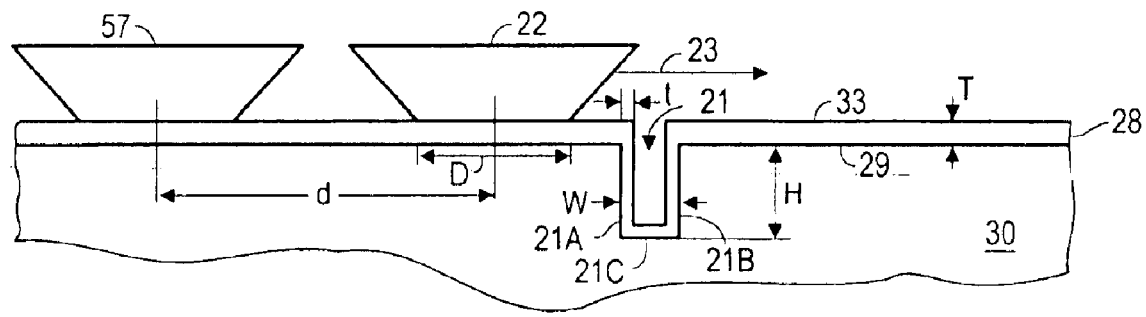
FIGS. 12 and 13 illustrate, in cross-sectional views, use of two beams in the embodiment of FIG. 11, with a first beam heating the semiconductor wafer and a second beam used to measure a change in reflectance due to heat from the first beam transferring through a feature.
Figure 13:
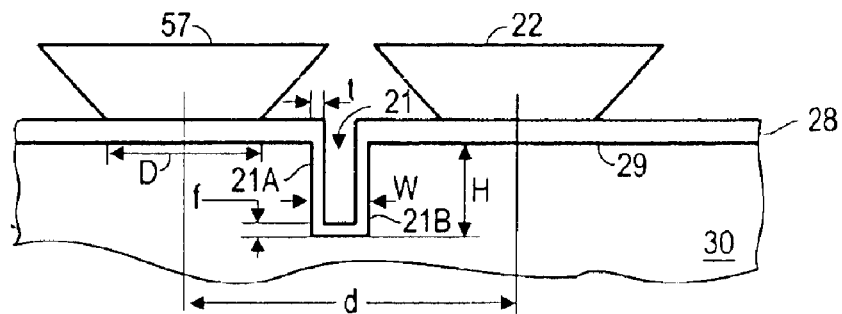

In one embodiment that uses two beams, wafer 20 is illuminated with two beams 57 and 22 (FIG. 12) that form spots (see acts 51 and 52 in FIG. 11) that are separated from one another by a fixed distance of separation d (see FIGS. 12 and 13). Beams 57 and 22 are focused on coplanar surfaces in this embodiment, although measurements of the type described herein can also be made with beams 57 and 22 focused on non-coplanar surfaces, e.g. as long as a thermal wave is not generated by an excessively high modulation frequency as described elsewhere herein.

Intensity of probe beam 22 reflected by wafer 20 is measured, with the spots on the same side of a feature to be evaluated (see act 53 in FIG. 11; see also FIG. 12) and on different sides of the feature (see act 54 in FIG. 11; see also FIG. 12). A difference in intensity measurements in acts 53 and 54 is indicative of a property of the feature, which affects a temperature gradient that is formed in a horizontal direction between the two spots. Specifically, a layer 28 of conductive material in the feature extends outwards from the feature, so that in act 53 when beam 22 forms a spot in a region adjacent to the feature, heat injected by beam 57 travels for distance d (which is the separation distance) through layer 28, and is sensed by measuring a reflected portion of beam 22.

Figure 14:
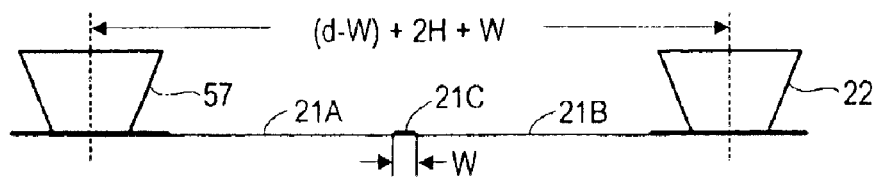
FIG. 14 illustrates a model for heat transfer in the configuration of FIG. 13.

Typical dimensions are a spot separation distance of d=4 μm, a groove depth of H=0.5 μm, a groove width of W=0.2 μm, a field layer thickness of T=1000 Å, a sidewall thickness of t=200 Å, and a floor thickness of f=400 Å (see FIG. 13). In act 54, when beams 57 and 22 are on opposites sides of a feature, heat under probe beam 22 must pass through a length (d-W) of layer 28, H of sidewall 21A, W of floor 21C and H of sidewall 21B, the combination of which may be modeled as illustrated in FIG. 14. The thinner coating H of sidewalls 21A and 21B has a greater impedance to the heat flow, and therefore its thickness governs the peak temperature. The thermal resistance can be modeled in a linear heat flow model:

$$R \propto \frac{d-W}{T_T} + \frac{W}{T_B} + \frac{2H}{T_w}$$

where $T_T$, $T_B$, and $T_W$ are the thickness of the conductive material on the top, bottom and sidewalls, d is the separation between the spots, W is the groove width, and H is the height of the sidewalls. Note that d>>W and both H>W and $T_B$>$T_W$, so the middle term is small compared to the first and last terms (the top and sidewall terms). The top and sidewall terms are comparable. However, the beam separation d is fixed and known and the top thickness $T_T$ can be determined independently by placing both spots on the top film without the intervening groove (in which case the R, and, hence, the heat rise under the probe beam 22, is now given by the first term since (d-W)~=d for d>>W). Therefore, the sensitivity of R to sidewall thickness $T_W$ can be found assuming a constant groove depth H.

In one implementation, the intensity of heating beam 57 (FIGS. 12–14) is modulated at a predetermined frequency, so that the temperature at the spot of probe beam 22 varies in synchronization with the modulation. The frequency is chosen to be sufficiently low to avoid creation of a thermal wave as described elsewhere herein and in the related patent applications Ser. No. 09/095,805 and 09/521,232 that were incorporated by reference above. Thereafter, reflectance is measured, by measuring intensity (referred to as measurement $S_f$) of a portion of the probe beam that is reflected by wafer 20, and that is modulated at the predetermined frequency. The modulated electrical signal is detected by use of a lock-in amplifier as stated in the just-described patent applications.

Figure 15:
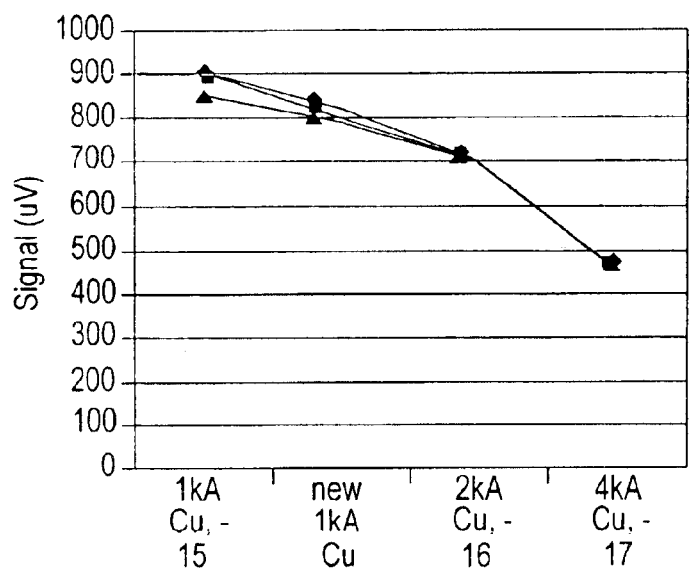
FIGS. 15 and 16 illustrate calibration curves used to look up properties of a feature in accordance with the method of FIG. 11.
Figure 17:
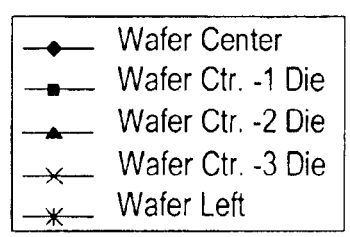
FIG. 17 provides a key for the graphs in FIGS. 15 and 16.

Measurement $S_f$ is proportional to the temperature under probe beam 22. When the spots are formed on the same side of a groove, measurement $S_f$ is converted using a calibration table obtained from independent measurement (under the same conditions) on layers (also called "films") of known thickness, thereby to determine the thickness T of layer 28. Therefore, a graph (not shown) may be used to look up thickness T (alternatively measurements used to form such a graph may be used directly by a computer to determine thickness T, e.g. by interpolation). Instead of using graphs and/or measurements, the above-described first term can also be used to determine thickness T. FIG. 15 shows signal for both beams on the same side of the groove (no thermal impedance due to the groove). In this case, the signal is expected to decline with metal thickness. This is because at constant laser power, the temperature to which the metal can be heated varies inversely with the metal thickness. Therefore, thicker films cannot be heated as much, and the signal is lower. This trend is seen in FIG. 15 for four wafers. The first two have target copper thicknesses of 1000 Å. The third has a thickness of 2000 Å, and the fourth 4000 Å.

Figure 16:
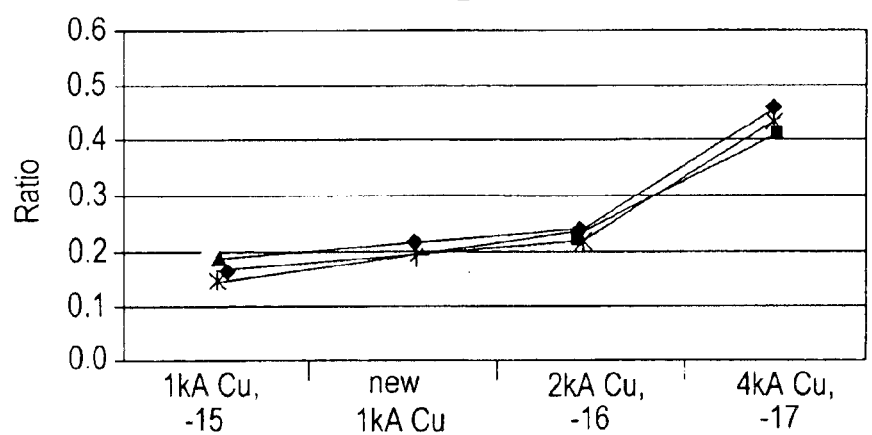

Next, while keeping the distance d between beams 57 and 22 fixed, the two beams are moved relative to wafer 20, to place the spots on a site where a groove passes between the two spots, and the reflected portion of beam 22 is measured, thereby to yield measurement $S_g$. Thereafter, a ratio of the previous measurement $S_f$ to the current measurement $S_g$ is used to look up the sidewall thickness, e.g. from a graph (which is obtained from independent measurement (under the same conditions) on grooves of known sidewall thickness). As before, alternatively the above relation (or a similar but more exact solution), with estimates of the groove height H, width W, and bottom thickness $T_B$ may be used to extract the sidewall thickness t. FIG. 16 show measurement identical to the one in FIG. 15, but with a 0.2 μm wide, 0.5 μm deep groove interposed between the two beams. The heating signal is normalized to the signal obtained without the groove to correct for the different temperatures to which the film can be heated, which is a function of the film thickness. This normalization is found by measuring with both beams placed on one side of the groove. The normalized signal with the groove between the two beams is called the "ratio". The ratio increases with thickness in the field because the thicker copper samples also have thicker sidewalls, so that the thermal impedance of the sidewalls is lower and more heat is conducted from the first beam to the second.

The measurement may be used to determine the sidewall thickness for a given groove dimension (width, depth) by correlating the measured ratio to a separate measurement of sidewall thickness obtained with any method well known in the art.

Alternately, this measurement may be used for process control. Consider the two samples labeled 1kA Cu and new 1kA Cu. These have the same nominal films, but the films differ due to process variation. A lower ratio indicates a thinner sidewall thickness. In the case shown here, a lower control limit of ratio=0.15 can be set and an upper limit of 0.25. Films measured in this ratio range are accepted; films outside this range are rejected.

Note that embodiments described above may be used in combination as follows. One embodiment measures the average sidewall thickness and another embodiment measures the asymmetry, showing the relative coverage of the two walls. The combination indicates that the average thickness is within the proper range. The asymmetry measurement indicates that the average thickness is not in the acceptable range because the coating is too thick on one wall and too thin on the other. The asymmetry is correlated empirically, by measuring the slope 32R and 32L. Acceptable values are set based on measurements using TEM or SEM, or other prior art methods.

Figure 18A:
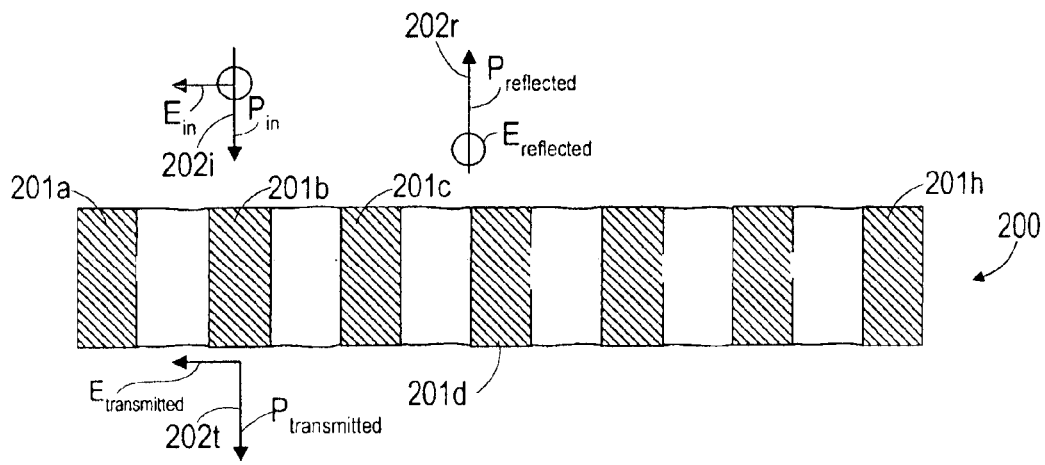
FIGS. 18A and 18B illustrate use of a beam polarized perpendicular to two types of array structures, to measure a property thereof, in another embodiment of the invention.

Another embodiment evaluates a wafer 20 having an array of metal lines 200, with the lines labeled 201a–h. Although the word "metal" is used, it is to be understood that lines 200 can be formed of any conductive material. FIG. 18A illustrates the cross-section of lines 200, which is assumed to extend along an axis perpendicular to the plane of the paper. Array 200 is illuminated with a beam 202i of power Pin, which may be composed of electric field components parallel and perpendicular to lines 201a–h. In FIG. 18A, the parallel component of beam 202i is shown as a circle and the perpendicular as an arrow Ein. The array line width is shown equal to the spacing (although this is not a constraint on the measurement) and the periodicity is smaller than the wavelength of the incident beam 202i.

When illuminated by a beam 202i, array 200 transmits a portion 202t and reflects another portion 202r, wherein the portions being reflected and transmitted depend on the respective polarization directions, as discussed above. Specifically, array 200 behaves in a manner similar or identical to a wire grid polarizer as described in the above-referenced U.S. patent application Ser. No. 09/521,232 and in Handbook of Optics at pages 10–72 to 10–77, which pages are incorporated by reference herein in their entirety. However, unlike the conventional use of wire grid polarizer to polarize radio waves and far-infrared radiation, this embodiment uses array 200 to polarize near-infrared or visible light of either or both of beams 57 and 22.

Figure 18B:
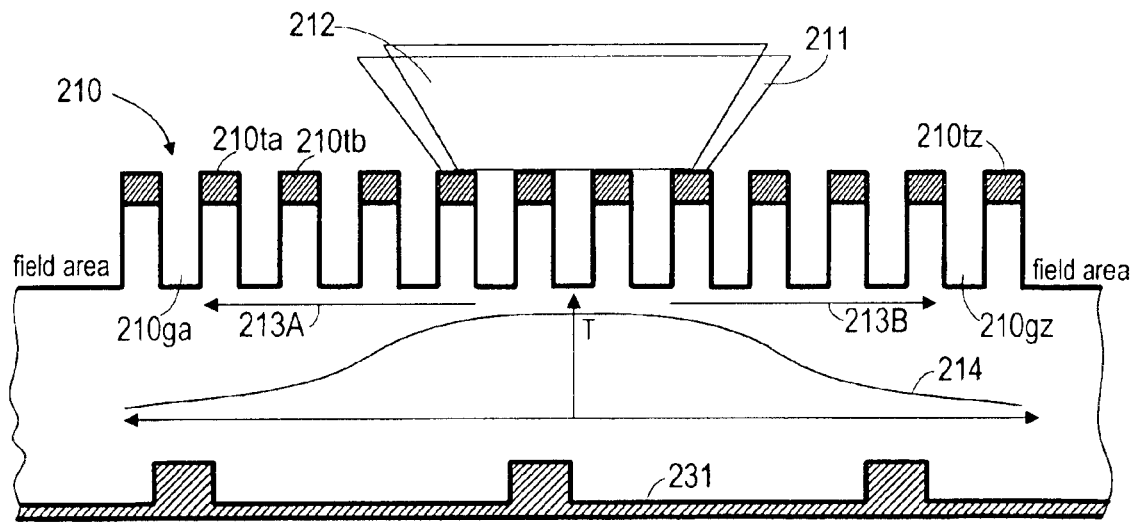

In accordance with the invention, the principle of wire grid polarizer can be extended to grooves that are completely coated with a conductor such as a metal, such as structure 210 illustrated in FIG 18B, which may be form by blanket deposition of metal on an area that is surrounded by field areas. The extension of the principle of wire grid polarizer to a completely coated array 210 is unexpected for at least two reasons. First, the metal electrically connects the adjacent grid elements, unlike a wire grid polarizer. Second, light that would normally pass through structure 210 (polarized perpendicular to the grid elements) now has nowhere to go at the bottom, because the bottom is closed by layer 231. Note that it is possible to employ the grooves of structure 210 as optical waveguides. The perpendicular polarization direction allows light to enter the grooves, exciting waveguide modes. This excitation provides the ability to selectively heat within the grooves, providing a temperature increase that is a function of the sidewall thickness, in part because the sidewalls provide a thermal impedance to heat flow out of the grooves that varies inversely with sidewall thickness. This energy sets up a temperature profile 214 as illustrated in FIG. 18B.

Figure 19A:
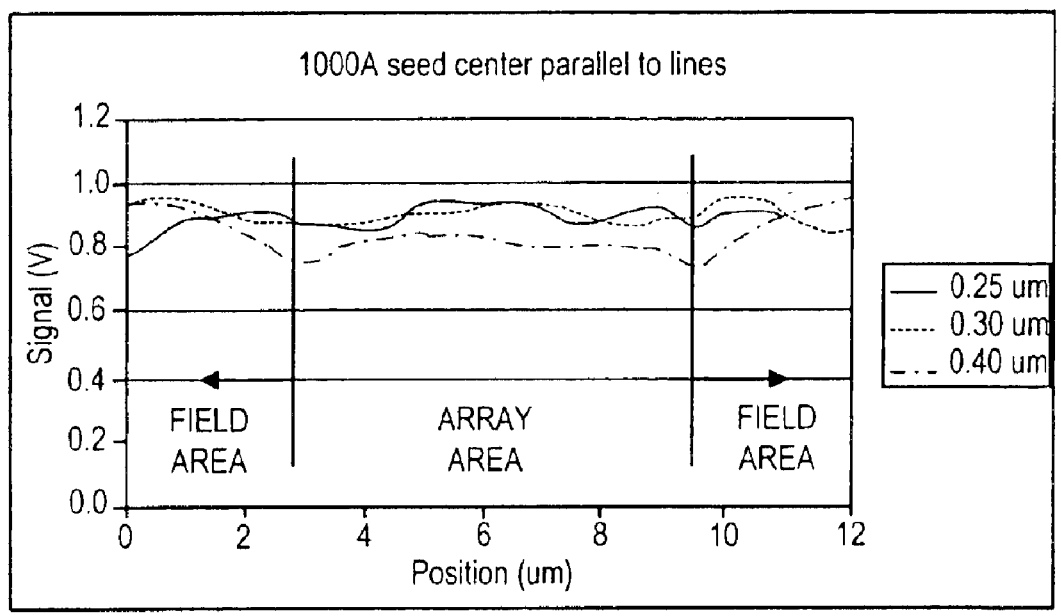
FIGS. 19A and 19B illustrate, in graphs, reflectance from the array structure of FIG. 18B, when the beam is respectively polarized parallel to, and perpendicular to the longitudinal direction of the array.

Under the above-described conditions, transmission properties of structure 210 are similar to those observed with array 200, wherein lines 201a–201f are independent of one another, as shown in FIG. 18A. Specifically, FIG. 19A shows the reflection signal in volts for 1 micron wavelength laser light as a 2 μm diameter spot is scanned across an array of grooves with trench widths from 0.25 to 0.40 μm coated from the top with 250 Å of Ta and 1000 Å of Cu. The arrays are 5 μm wide, so each scan begins on the left side field area, passes over the array area, and ends on the right side field area.

Figure 19B:
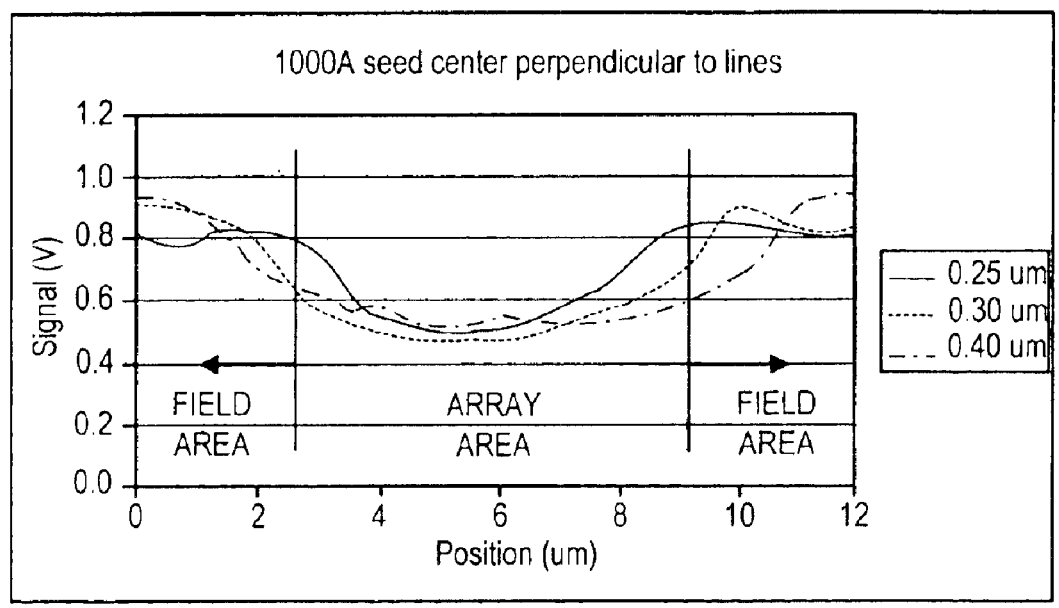

Note that there is no significant change (e.g. less than 20%) in reflection during the scan when using parallel polarization (FIG. 19A). Thus, the array area reflects substantially like the field area, as seen with the wire grid. However, the same experiment done with perpendicular polarization of the probe beam shows a dip (e.g. reduction by more than 20%) in reflection in the array area (in comparison to the field area), as seen in FIG. 19B. The magnitude of the dip provides an indication of the aspect ratio, as discussed next.

As illustrated by FIGS. 19A–19B, use of parallel polarization of heating beam 57 results in reflection from the tops of the grooves, with very little light (e.g. less than 20%) leaking into the grooves. Conversely, use of perpendicular polarization of heating beam 57 results in light passing into the grooves, where at least a portion of the non-absorbed light is absorbed to heat the groove walls (some fraction may transmit through the groove walls, since the metal on the walls may be thinner than the skin depth of the metal). Furthermore, light within the grooves is more effectively absorbed, since the grooves being deep and narrow (e.g. aspect ratio >2) act as light traps.

Therefore, a measurement of sidewall thickness t is made in one implementation in the following manner:

1. Light polarized perpendicular to the grooves is shone onto the corrugated structure 210, becomes absorbed and converted to heat; this heats the structure to a temperature inversely proportional to the sidewall thickness.

2. A second laser polarized parallel to the grooves is shone on the structure 210; due to its polarization, it only reflects from the tops of the grooves; alternatively second laser is polarized perpendicular to the grooves, and is reflected by the sidewalls.

3. The reflectance is a function of temperature, so the reflection of the second laser is a measure of sidewall coverage.

Specifically, laser beam 211 (FIG. 18B), which forms a heating beam of this embodiment, is polarized perpendicular to the axis of the grooves in structure 210. Structure 210 has groove floors 210ga, 210gb . . . 210gz, tops 210ta, 210tb . . . 210tz and sidewalls therebetween. Because of the polarization of beam 211, it pumps heat into the grooves (which include the sidewalls and the groove floors). This heat diffuses out of the illuminated region, to the cooler adjacent regions, as shown by the arrows 213A and 213B. This diffusion sets up a temperature profile 214 which is hottest at the center and cooler with distance from the laser beam 211.

With respect to the absorption of light in the grooves, the typical case, in fact, is a cross between the two structures 200 and 210 shown in FIGS. 18A and 18B, the one extreme being that the metal lines are isolated and there is a transmission path through structure 200 for light polarized perpendicular to the lines, and the other being the case of a thick metal coating that makes structure 210 completely opaque. The case typically is intermediate because the thickness of the metal on the sidewalls is on the order of the skin depth, that being the thickness at which the light intensity decays to 1/e due to absorption within the metal. For a wavelength of 0.83 μm, the 1/e absorption distance for copper is 125 Å, and for a barrier metal such as tantalum the 1/e absorption distance is 176 Å.

The temperature profile 214 (FIG. 18B) is governed by the thickness t of the sidewall coating (also called simply "sidewall"), because: first, the thickness of the tops 210ta–210tz is uniform and independent of variation in groove properties, since the deposition on the tops 210ta–210tz is in direct view of the deposition source; second, the thermal path through the groove floors 210ga–210gz is much longer than the path through the tops 210ta–210tz (for 0.5 μm deep grooves with half-pitch of 0.2 μm, the path length through the tops 210ta–210tz is 0.2 μm and through the groove floors 210ga–210gz is 1.2 μm); and third, the coating in the grooves is much thinner, and the thermal impedance is inversely proportional to the metal thickness. For example, the thickness on the tops 210ta–210tz may be 0.1 μm and in the grooves 0.02 μm. In this case, the thermal impedance in the path through the grooves is 30 times than through the tops, so that the temperature profile is substantially governed by the sidewall thickness t.

Heat also flows along the length of the grooves and tops (i.e in the longitudinal direction, which is perpendicular to the plane of the paper in FIG. 18B). In this case, the cross section of the metal in the grooves (including the sidewalls and the floor) is about equal to the cross section at the top, so the heat flow in this axis is equally divided between the tops and the grooves, and the sidewall thickness variation contributes to about half of the temperature drop in this axis. Because the structure 210 is embedded in an insulator, parasitic heat leakage through conduction paths other than the metal does not adversely affect the measurement.

The peak temperature is measured using a second laser beam 212, which forms a probe beam of this embodiment. Laser beam 212 is polarized either parallel or perpendicular to the grooves, depending on the implementation. When polarized parallel, laser beam 212 only reflects from the tops, thereby making its reflection independent of the groove properties. The reflectance of any metal is a function of temperature, so the reflection of parallel polarized beam 212 is a measure of the temperature profile of the tops, which in turn is governed by the sidewall thickness. Hence the measurements provide an indication of sidewall thickness.

Figure 20:
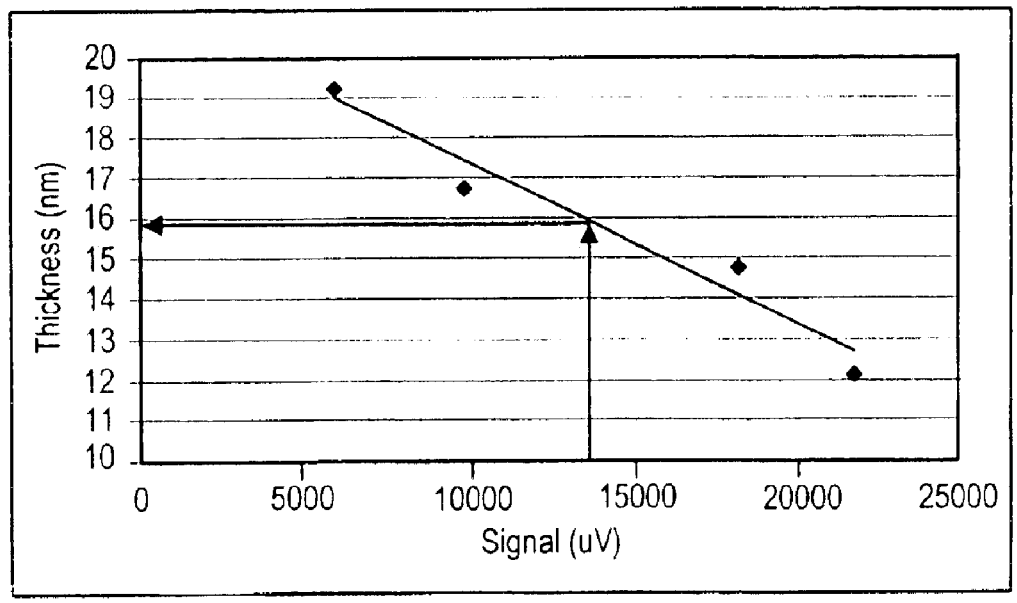
FIGS. 20 and 21 illustrate, use of a predetermined curve to lookup thickness of a sidewall, based on a measure of reflectance of probe beams that are parallel polarized and perpendicular polarized respectively.

FIG. 20 presents measurements from a set of grooves with pitches ranging from 0.5 to 0.8 μm, the groove width being half the pitch. The grooves are 0.5 μm deep. The structures are completely coated with 250 Å of Ta and 1000 Å of Cu, and the sidewall coverage is a function of the width of the grooves (since the metal is impeded from coating the walls by virtue of the high aspect ratio). During calibration, the coverage is also measured independently, by any well known method, e.g. by sectioning the grooves using a focused ion beam and then imaging the cross-section with a scanning electron microscope. The graph in FIG. 20 provides a calibration curve for use in process control. Once it has been obtained, the correlation line (FIG. 20) is used to calibrate the signal to the sidewall thickness. For example, a signal of 13,000 units corresponds to a sidewall coverage of 15.9 nanometers.

Figure 21:
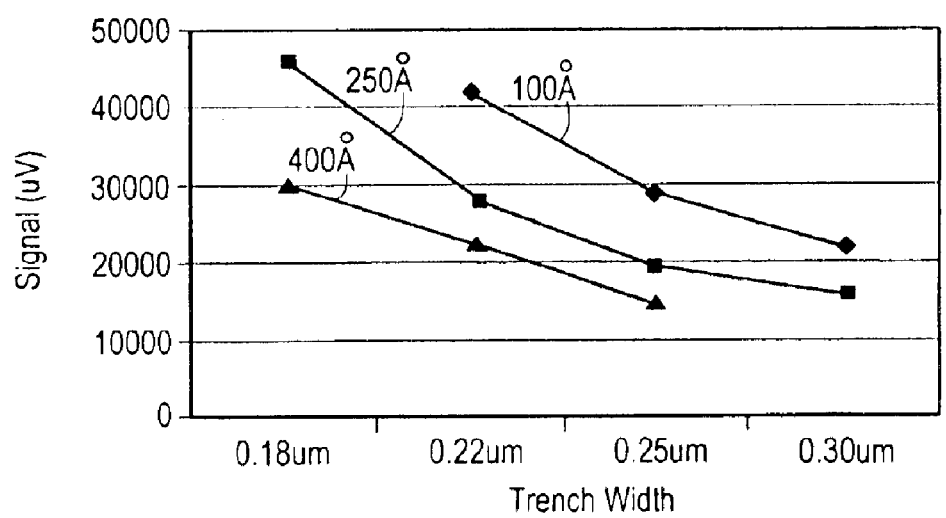

In an alternative embodiment, laser beam 211 is polarized perpendicular to the grooves, and is therefore reflected by sidewalls and groove floors of array 210. As the sidewalls and floors are heated, the reflected portion of such a perpendicular polarized beam 211 also provides a measure of the temperature profile, and, hence, sidewall thickness. The measurement using perpendicular polarized beam 211 is more accurate and more sensitive than a corresponding measurement using parallel polarized beam 211. The graph in FIG. 21 provides a calibration curve for use in process control, based on use of perpendicular polarized beam 211.

Figure 22:
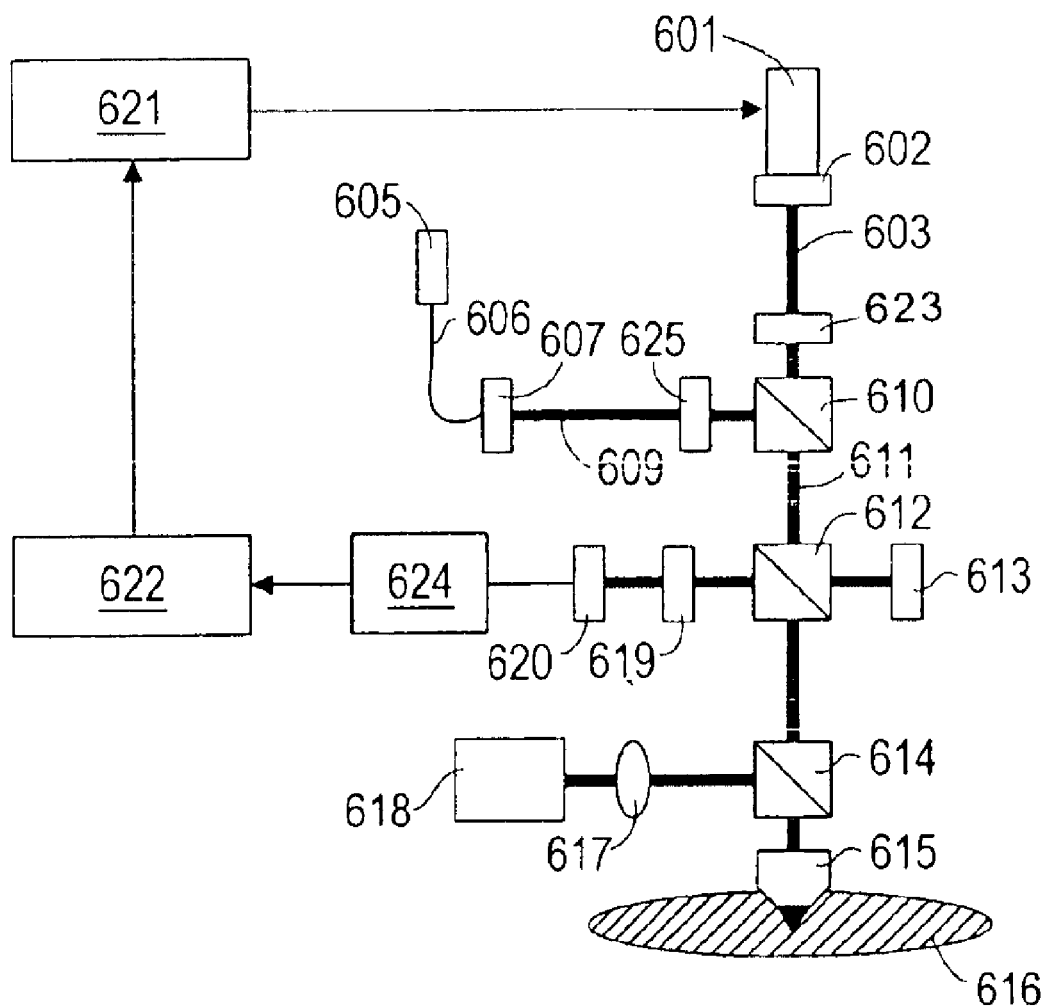
FIG. 22 illustrates a measurement apparatus in one embodiment.

FIG. 22 shows one implementation of a measurement apparatus in accordance with the invention. A first laser 601 has a wavelength of 830 nm and a maximum output power of 100 mW (Spectra Diode Laboratories model 2300). Collimating lens 602 forms a four mm diameter collimated beam 603 that is linearly polarized by virtue of the laser's output characteristics. The polarization direction may be optionally rotated using half-wave plate 623 to align the direction relative to a pattern of lines on the wafer. Half-wave plate 623 may be mounted on an actuator to be placed in or out of the beam. Beam 603 is referred to as the "heating beam," and is used to heat the measured area.

Second laser 605 is a semiconductor diode laser with a wavelength of 980 nm (Spectra Diode Laboratories model 6700). It is coupled to the system using optical fiber 606, and the beam is collimated using lens 607, providing a 4 mm diameter circularly polarized beam 609. Beam 609 is linearly polarized using quarter-wave plate 625. Beams 609 and 603 are combined using dichroic mirror 610, forming single combined beam 611. Beam 611 passes through beam splitter 612, whose purpose is to send the return beam to the detector. A portion of beam 611 is detected using photocell 613, which may be used to ensure proper calibration of the power of beam 611. Beam 611 then passes through beam splitter 614 and focusing lens 615, which is a 100× lens (Olympus, Tokyo Japan), focusing the combined beam on the wafer 616.

The reflected light is re-collimated with lens 615. 90:10 beam splitter 614 diverts the return beam 611 to an autofocus and imaging system consisting of lens 617 and camera 618 (an additional beam splitter, pinhole and detector for the autofocus are not shown). Lens 617 and camera 618 enables viewing of the sample to place the focus spot at the correct location. The autofocus system allows the focus spot of the laser beams to be maintained at the surface of the wafer 616. Half of the power in beam 611 is then sent to optical narrow-band filter 619, which passes the light from laser 605 (980 nm) but blocks the light from laser 601 (830 nm). The transmitted light passes to photodetector 620, amplifier 624, and lock-in amplifier 622. The signal from lock-in amplifier 622 is then sent to a computer for analysis.

Lock-in amplifier 622 has a oscillator that serves as a reference signal for synchronous detection of the output of photocell 620 and amplifier 624. This oscillator is used as an input to laser driver 621, which provides a modulated drive for laser 601. The modulation frequency is preferably <2 KHz. This is to avoid creation of thermal waves. Such waves are generated at higher modulation frequencies. Because of the uneven (corrugated) geometry of structure 210, any waves will cause reflections that will confuse the measurement, and must therefore be rigorously avoided.

Filter 19 is on an actuator so that it may be removed to enable use of laser 601 for single beam measurement. In this case, laser 605 is turned off, e.g. by closing a shutter.

The heat flow obeys the diffusion equation, which in its simplest form (one-dimension) is $$\frac{\partial^2 T}{\partial x^2} + \frac{Q}{K} = \frac{1}{\alpha}\frac{\partial T}{\partial t} \quad (1)$$

where T is the temperature rise above ambient, Q is the heat input per unit volume, K is the thermal conductivity, and a is the thermal diffusivity. Under sinusoidal excitation, the temperature is written as $T(z,t)=T(z)e^{j\omega t}$ where $\omega=2\pi f$ and f is the excitation frequency. In the region outside the heating spot, Q=0, and equation (1) is written as $$\frac{\partial^2 T}{\partial x^2} - j\frac{\omega}{\alpha}T = 0 \quad (2)$$

which has a solution of the form $$T(z) = T_0 \exp\left[(1+j)\left(\sqrt{\frac{\pi f}{\alpha}}\right)z\right],$$

which is a decaying wave with a wavelength $$\lambda = \sqrt{\frac{\alpha}{\pi f}}.$$

The criterion for a "steady-state" measurement—that is, a measurement without the presence of an unwanted wave component—is $\lambda\gg L$, where L is the length of the structure that is being measured, or, alternately, the length over which the temperature profile decays because of heat loss mechanisms such as diffusion into the insulator underneath the metal film. This sets up a relationship for the modulation frequency of $$f \ll \frac{\alpha}{\pi L^2} \quad (3)$$

Figure 23:
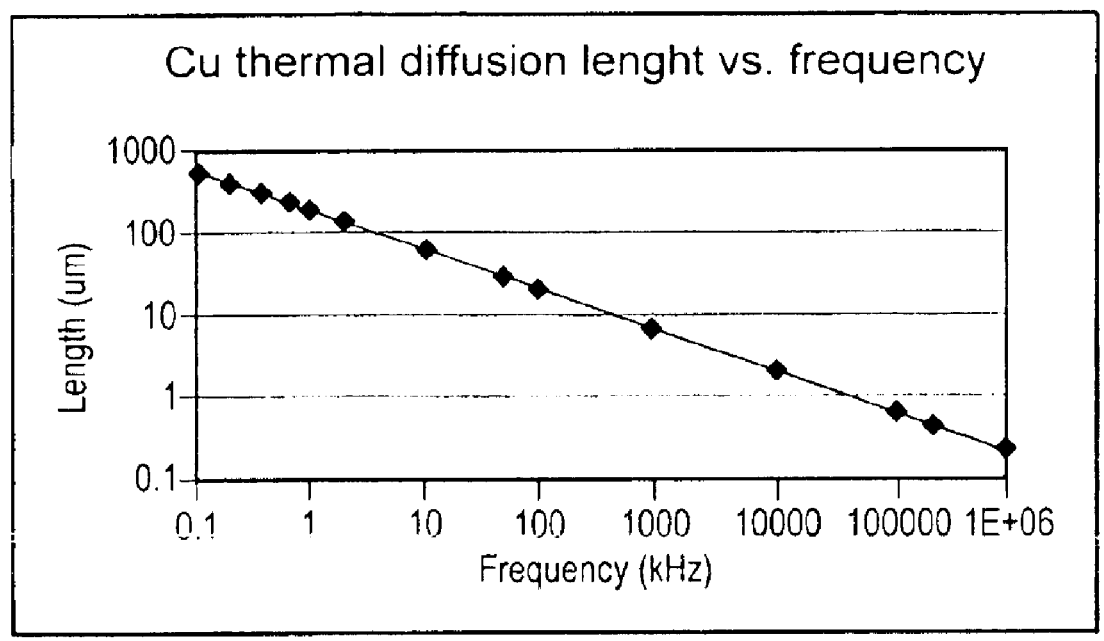
FIG. 23 illustrates, in a graph, a relationship between modulation frequency and thermal wavelength.

FIG. 23 shows a graph of the frequency versus the length L. When L is on the order of 10 μm, the condition of equation (3), to avoid generation of a thermal wave, is met when the frequency is less than 10 KHz.

Figure 24:
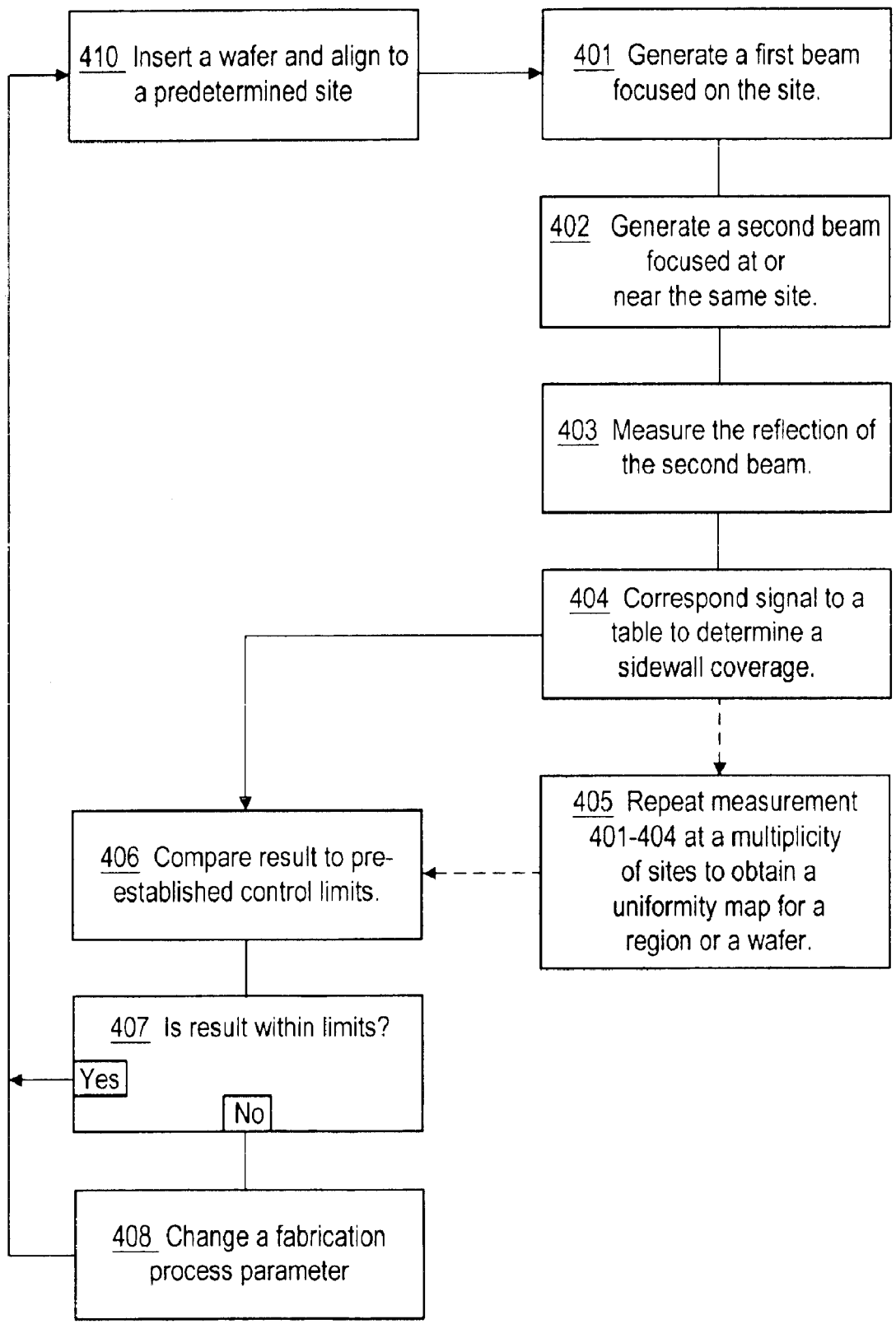
FIG. 24 illustrates in a flow chart, acts performed as described herein for performing process control.

FIG. 24 provides a flow chart of how the measurement is used for process control. In step 410 a wafer is inserted into the measurement system and aligned to a predetermined site. In step 401 the first heating beam is focused at the predetermined site. In step 402 the second measurement beam is focused on the same predetermined site. In step 403 the reflection of the second beam is measured to provide a signal. In step 404 the signal is corresponded to a predetermined value using a look-up table or a correlation function. This provides a sidewall coverage value. At this point, in step 405 the result may be stored and steps 401–404 may be repeated at other sites to provide a map of a region or of multiple sites on the wafer. The results of steps 404 or 405 are compared to predetermined control limits to see if the sidewall coverage is within the proper specification. If it is, the wafer is sent to the next process step and the measurement sequence is repeated on a new wafer. If it is not, an in step 408 an appropriate fabrication process parameter is changed and applied to the processing of further wafers, which then enter step 410 for measurement.

Figure 25:
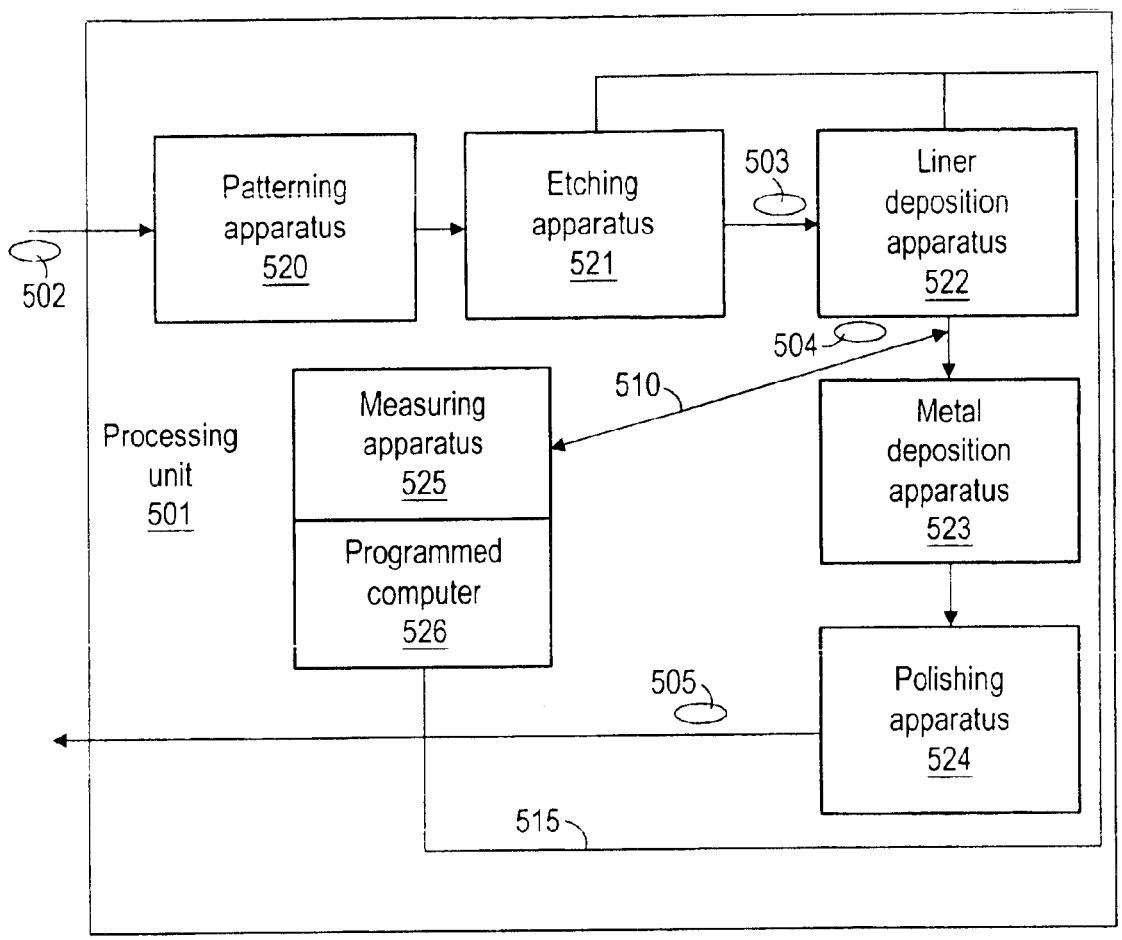
FIG. 25 illustrates a system for fabricating wafers using a reflectance measurement as described herein.

FIG. 25 shows a block diagram of how the measurement is implemented as part of a damascene interconnect process flow. The process flow consists of passing a wafer 502 through a number of sequential process tools, including patterning apparatus 520, etching apparatus 521, etching apparatus 521, liner deposition apparatus 522 (which deposits the barrier and seed layers, the combination of which is called the liner), metal deposition apparatus 523, polishing apparatus 524, and measuring apparatus 525, which includes a programmed computer 526. Wafer 502 is shown entering the liner deposition as wafer 503 and exiting as wafer 504. In path 510 wafer 504 is measured using the flow chart sequence shown in FIG. 7.

If the measurement is within limits, the wafer is returned to the process flow for the next step, eventually being completed as wafer 505. If not, the programmed computer sends, using connection 515, a signal to the etching and liner deposition machines to make predetermined adjustments. Numerous modifications and adaptations of the above-described embodiments, implementations, and examples will become apparent to a person skilled in the art of using lasers to measure properties of semiconductor wafers. For example, in an alternative embodiment, instead of using a laser to generate a heating beam, another heat source (such as an electron gun and electron focusing column that forms an electron beam) is used to modulate the temperature T. Also, a probe beam used to measure the sidewall thickness as described herein can consist of x-rays.

For example, although in the embodiment illustrated in FIGS. 18A and 18B, heating beam 211 forms a spot that overlaps a corresponding spot formed by probe beam 212, such measurements can also be performed with the spots being separated by a fixed distance, e.g. if the spots are formed on the feature being evaluated (aligned in the longitudinal direction) and if heating beam 211 is modulated. Moreover, although a polarized probe beam is described for use in the embodiment illustrated in FIGS. 18A and 18B, an unpolarized probe beam may be used in another embodiment.

In another example, a sidewall thickness measurement is made using two lasers, both polarized perpendicular to a groove, and following the sidewall thickness measurement, one laser is turned off and the wafer is scanned under the remaining laser beam. The symmetry of the scan is then observed to verify that the sidewall coating is even (i.e. has the same thickness) on both sides of the groove. In yet another example, one beam is not turned off and instead the two beams are scanned along the longitudinal direction of the feature, thereby to provide a linear scan in terms of the sidewall thickness.

Moreover, structures other than semiconductor wafers (e.g., photomasks that include a glass substrate and are used to form the wafers, or an active matrix liquid crystal display) can also be evaluated as described herein.

Furthermore, instead of scanning as described herein, another embodiment performs hopping. Specifically, this embodiment involves a stepwise movement ("hopping") from one region to another region of the wafer when performing measurements of the type described herein (as opposed to scanning that continuously moves ("sweeps") the beam of electromagnetic radiation relative to the wafer. In the hopping process, the stage holds the wafer stationary for a moment (e.g., 1 second) while a measurement is taken in one region, and then moves to another region (e.g., of the same wafer).

Two regions in which measurements are made can be separated from each other, e.g., by distance which is same as the diameter of the beam. Alternatively, the two regions can touch each other or even overlap each other. When overlapping one another, the centers of the two regions may be separated by a small fraction of the diameter, e.g., by ($\frac{1}{10}$) D or less. Regardless of how close the regions are, the hopping process yields discrete values (one for each region) as compared to the sweeping process which yields a continuous signal. As described elsewhere herein, the regions can be physically located on different features (e.g. on the two sidewalls of a groove), so that an alternative embodiment involves hopping from feature to feature (when hopping among features). A combination of the just-described two types of hopping can also be used (i.e., moving between regions of the same feature and also moving between features).

Note that the just-described "hopping" can be performed from one region to a next region that touch each other, and a measurement from each region can be plotted in a graph, e.g., to indicate a profile of sidewall thickness across the regions. In another embodiment, hopping is performed between regions that overlap one another thereby to provide a more realistic measure of the average profile across these regions, as compared to non-overlapping regions.

Numerous modifications and adaptations of the above-described embodiments, implementations, and examples are encompassed by the attached claims.

What is claimed is:

1. A method of evaluating a feature in a semiconductor wafer, the method comprising:

illuminating the wafer with a beam of electromagnetic radiation having a majority of energy polarized in a selected direction, said selected direction being other than parallel to a longitudinal direction of the feature, wherein the wafer comprises a layer located between a source of the beam and the feature, the layer is at least partially transmissive, so that a portion of the beam passes through the layer, and the layer is thermally conductive; and measuring a change in reflectance of the feature due to heat transfer therethrough caused by illumination with the beam.

2. The method of claim 1 wherein:

the feature includes a sidewall of a groove; and the act of measuring is performed repeatedly at a plurality of locations transverse to the longitudinal direction of the groove.

3. The method of claim 2 wherein:

the beam has a wavelength greater than thickness of the sidewall.

4. The method of claim 1 wherein:

the beam has a wavelength greater than a dimension of the feature; and the beam forms on the wafer a spot of a diameter greater than the dimension.

5. The method of claim 1 wherein:

the feature includes a trace of reflective material.

6. The method of claim 1 wherein:

the selected direction is at least substantially perpendicular to the longitudinal direction.

7. The method of claim 1 wherein:

the beam has a predetermined wavelength; and the method further comprises filtering light of a wavelength other than the predetermined wavelength.

8. The method of claim 1 wherein the wafer has a plurality of features including the feature, and the method further comprises:

performing the act of measuring for each feature of the plurality; and comparing measurements of multiple features.

9. The method of claim 8 wherein:

each feature is a sidewall; and the act of comparing includes comparing measurements of two sidewalls located opposite to one another in a groove.

10. The method of claim 1 further comprising:

forming the feature of conductive material in the wafer by using at least one process parameter;

repeatedly performing said measuring intensity; and changing the process parameter depending on measurements obtained from the act of repeatedly measuring.

11. A method of evaluating wafers during fabrication, the method comprising:

forming a feature of conductive material in a wafer by using at least one process parameter;

illuminating the wafer with a beam of electromagnetic radiation having a majority of energy polarized in a direction other than parallel to a longitudinal direction of the feature; and repeatedly measuring intensity of a portion of the beam reflected by the wafer at a plurality of locations transverse to the longitudinal direction;

changing the process parameter depending on measurements obtained from the act of repeatedly measuring;

determining a coefficient of a function that fits the measurements;

comparing the coefficient against a predetermined limit and performing the changing based on an outcome of the comparing.

12. The method of claim 11 wherein:

the feature includes a sidewall of a groove.

13. The method of claim 12 wherein the beam has a wavelength greater than thickness of the sidewall.

14. The method of claim 11 wherein:

the beam has a wavelength greater than a dimension of the feature; and the beam forms on the wafer a spot of a diameter greater than the dimension.

15. The method of claim 11 wherein:

the feature includes a trace of reflective material.

16. The method of claim 11 wherein:

the wafer includes a layer located between a source of the beam and the feature; and the layer is at least partially transmissive, so that the portion passes through the layer.

17. The method of claim 11 wherein:

the beam has a predetermined wavelength; and the method further comprises filtering light of a wavelength other than the predetermined wavelength.

18. The method of claim 11 wherein the wafer has a plurality of features including the feature, and the method further comprises:

performing the act of measuring for each feature of the plurality; and comparing measurements of multiple features.

19. The method of claim 11 wherein the beam is a first beam, and the method further comprises:

illuminating the wafer with a second beam of electromagnetic radiation.

20. The method of claim 19 wherein:

the first beam forms a first spot on the wafer, the second beam forms a second spot;

the act of measuring includes measuring with the first spot and the second spots located on opposite sides of the feature; and the method further comprises measuring with the first spot and the second spots located on the same side of the feature.

21. The method of claim 20 wherein:

the second spot at least partially overlaps the first spot.

22. A method of evaluating a groove in a semiconductor wafer, the method comprising:

illuminating the wafer with a beam of light polarized in a direction P, said direction P forming an angle $\theta$ with a longitudinal direction of the groove, with angle $\theta > 45°$;

wherein the beam has a wavelength larger than a width of the groove, the groove is formed of a highly reflective material, and the groove has a first sidewall, a second sidewall and a floor between the first sidewall and the second sidewall;

heating of the groove by a portion of the light polarized perpendicular to the groove, heat from said heating being transmitted into a substrate of the semiconductor wafer; and measuring intensity of light reflected by the wafer, wherein light absorbed in the groove measurably reduces the reflected light.

23. The method of claim 22 wherein:

using a measurement obtained from said measuring as an indication of a thickness of the sidewall.

24. The method of claim 22 wherein: with angle $\theta$ is approximately 90°.

25. The method of claim 24 wherein: said light reflected by the wafer is part of said beam.

26. The method of claim 24 wherein:

said light reflected by the wafer is part of another beam.

27. The method of claim 1 wherein:

said layer is metallic.

28. The method of claim 1 wherein:

said layer comprises copper.

29. The method of claim 1 wherein:

said layer comprises tantalum.

30. The method of claim 1 wherein:

said layer comprises a barrier layer.

31. The method of claim 1 wherein:

said layer comprises a seed layer.

32. The method of claim 11 wherein:

said conductive material comprises copper.

33. The method of claim 11 wherein:

said conductive material comprises tantalum.

34. The method of claim 11 wherein:

said conductive material forms a barrier layer during wafer fabrication.

35. The method of claim 11 wherein:

said conductive material forms a seed layer during wafer fabrication.

36. The method of claim 11 wherein:

said conductive material is metallic.

37. A method of evaluating a feature in a semiconductor wafer, the method comprising:

illuminating the wafer with a beam of electromagnetic radiation having a majority of energy polarized in a selected direction, said selected direction being substantially perpendicular to a longitudinal direction of the feature, wherein the wafer comprises a thermally conductive layer located between a source of the beam and the feature; and measuring intensity of a portion of the beam reflected at least by the thermally conductive layer.

38. The method of claim 37 wherein:

said thermally conductive layer comprises a barrier layer.

39. The method of claim 37 wherein:

said thermally conductive layer comprises a seed layer.

* * * * *